(12) United States Patent
Chen et al.

(10) Patent No.: US 10,047,118 B2
(45) Date of Patent: Aug. 14, 2018

(54) C17-ARYL SUBSTITUTED BETULINIC ACID ANALOGS

(71) Applicant: ViiV Healthcare UK (No.5) Limited, Brentford, Middlesex (GB)

(72) Inventors: Jie Chen, Wallingford, CT (US); Yan Chen, Wallingford, CT (US); Nicholas A. Meanwell, Wallingford, CT (US); Alicia Regueiro-Ren, Wallingford, CT (US); Ny Sin, Wallingford, CT (US); Sing-Yuen Sit, Wallingford, CT (US)

(73) Assignee: ViiV HEALTHCARE UK (NO.5) LIMITED, Brentford, Middlesex (GB)

( * ) Notice: Subject to any disclaimer, the term of this patent is extended or adjusted under 35 U.S.C. 154(b) by 0 days.

(21) Appl. No.: 15/523,453

(22) PCT Filed: Nov. 12, 2015

(86) PCT No.: PCT/US2015/060353
§ 371 (c)(1),
(2) Date: May 1, 2017

(87) PCT Pub. No.: WO2016/077569
PCT Pub. Date: May 19, 2016

(65) Prior Publication Data
US 2017/0305962 A1    Oct. 26, 2017

Related U.S. Application Data

(60) Provisional application No. 62/079,966, filed on Nov. 14, 2014.

(51) Int. Cl.
*C07J 63/00*    (2006.01)
(52) U.S. Cl.
CPC .................. *C07J 63/008* (2013.01)
(58) Field of Classification Search
CPC .................................................. C07J 63/008
See application file for complete search history.

(56) References Cited

U.S. PATENT DOCUMENTS

2005/0014730 A1*    1/2005    Carlson et al.

FOREIGN PATENT DOCUMENTS

| WO | 2009073818 A1 | 6/2009 |
| WO | 2012106190 A1 | 8/2012 |
| WO | 2013117137 A1 | 8/2013 |
| WO | 2013160810 A2 | 10/2013 |

OTHER PUBLICATIONS

HIV Vaccines [online]. Retrieved from the internet on Jul. 6, 2017 URL: <http://www.hiv.gov/hiv-basics/hiv-prevention/potential-future-options/hiv-vaccines>.*
HIV Vaccine: How Close Are We? [online]. Retrieved from the internet on Jul. 6, 2017 URL: <http://www.healthline.com/health/hiv-aids/vaccine-how-close-are-we>.*

* cited by examiner

*Primary Examiner* — Shawquia Jackson
(74) *Attorney, Agent, or Firm* — Robert H. Brink; Edward R. Gimmi; William R. Majarian

(57) ABSTRACT

Compounds having drug and bio-affecting properties, their pharmaceutical compositions and methods of use are set forth. In particular, betulinic acid derivatives that possess unique antiviral activity are provided as HIV maturation inhibitors, as represented by compounds of Formula I:

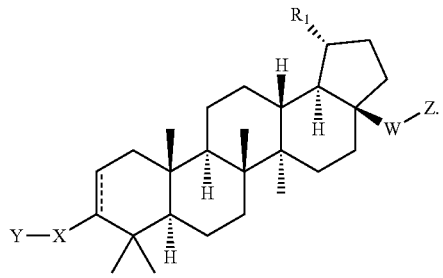

Formula I

These compounds are useful for the treatment of HIV and AIDS.

7 Claims, No Drawings

C17-ARYL SUBSTITUTED BETULINIC ACID ANALOGS

CROSS REFERENCE TO RELATED APPLICATION

This application is a § 371 of International Application No. PCT/US2015/060353, filed 12 Nov. 2015, which claims the benefit of U.S. Provisional Application No. 62/079,966, filed 14 Nov. 2014, which are incorporated herein in their entireties.

FIELD OF THE INVENTION

The present invention relates to novel compounds useful against HIV and, more particularly, to compounds derived from betulinic acid and other structurally-related compounds which are useful as HIV maturation inhibitors, and to pharmaceutical compositions containing same, as well as to methods for their preparation.

BACKGROUND OF THE INVENTION

HIV-1 (human immunodeficiency virus-1) infection remains a major medical problem, with an estimated 45-50 million people infected worldwide at the end of 2010. The number of cases of HIV and AIDS (acquired immunodeficiency syndrome) has risen rapidly. In 2005, approximately 5.0 million new infections were reported, and 3.1 million people died from AIDS. Currently available drugs for the treatment of HIV include nucleoside reverse transcriptase (RT) inhibitors or approved single pill combinations: zidovudine (or AZT or RETROVIR®), didanosine (or VIDEX®), stavudine (or ZERIT®), lamivudine (or 3TC or EPIVIR®), zalcitabine (or DDC or HIVID®), abacavir succinate (or ZIAGEN®), Tenofovir disoproxil fumarate salt (or VIREAD®), emtricitabine (or FTC-EMTRIVA®, COMBIVIR® (contains −3TC plus AZT), TRIZIVIR® (contains abacavir, lamivudine, and zidovudine), EPZICOM® (contains abacavir and lamivudine), TRUVADA® (contains VIREAD® and)EMTRIVA®; non-nucleoside reverse transcriptase inhibitors: nevirapine (or VIRAMUNE®), delavirdine (or RESCRIPTOR®) and efavirenz (or SUSTIVA®), ATRIPLA® (TRUVADA®+SUSTIVA®), and etravirine, and peptidomimetic protease inhibitors or approved formulations: saquinavir, indinavir, ritonavir, nelfinavir, amprenavir, lopinavir, KALETRA® (lopinavir and Ritonavir), darunavir, atazanavir (REYATAZ®) and tipranavir (APTIVUS®) and cobicistat, and integrase inhibitors such as raltegravir (ISENTRESS®), and entry inhibitors such as enfuvirtide (T-20) (FUZEON®) and maraviroc (SELZENTRY®).

Each of these drugs can only transiently restrain viral replication if used alone. However, when used in combination, these drugs have a profound effect on viremia and disease progression. In fact, significant reductions in death rates among AIDS patients have been recently documented as a consequence of the widespread application of combination therapy. However, despite these impressive results, 30 to 50% of patients may ultimately fail combination drug therapies. Insufficient drug potency, non-compliance, restricted tissue penetration and drug-specific limitations within certain cell types (e.g. most nucleoside analogs cannot be phosphorylated in resting cells) may account for the incomplete suppression of sensitive viruses. Furthermore, the high replication rate and rapid turnover of HIV-1 combined with the frequent incorporation of mutations, leads to the appearance of drug-resistant variants and treatment failures when sub-optimal drug concentrations are present. Therefore, novel anti-HIV agents exhibiting distinct resistance patterns, and favorable pharmacokinetic as well as safety profiles are needed to provide more treatment options. Improved HIV fusion inhibitors and HIV entry coreceptor antagonists are two examples of new classes of anti-HIV agents further being studied by a number of investigators.

HIV attachment inhibitors are a further subclass of antiviral compounds that bind to the HIV surface glycoprotein gp120, and interfere with the interaction between the surface protein gp120 and the host cell receptor CD4. Thus, they prevent HIV from attaching to the human CD4 T-cell, and block HIV replication in the first stage of the HIV life cycle. The properties of HIV attachment inhibitors have been improved in an effort to obtain compounds with maximized utility and efficacy as antiviral agents. In particular, U.S. Pat. No. 7,354,924 and U.S. Pat. No. 7,745,625 are illustrative of HIV attachment inhibitors.

Another emerging class of compounds for the treatment of HIV are called HIV maturation inhibitors. Maturation is the last of as many as 10 or more steps in HIV replication or the HIV life cycle, in which HIV becomes infectious as a consequence of several HIV protease-mediated cleavage events in the gag protein that ultimately results in release of the capsid (CA) protein. Maturation inhibitors prevent the HIV capsid from properly assembling and maturing, from forming a protective outer coat, or from emerging from human cells. Instead, non-infectious viruses are produced, preventing subsequent cycles of HIV infection.

Certain derivatives of betulinic acid have now been shown to exhibit potent anti-HIV activity as HIV maturation inhibitors. For example, U.S. Pat. No. 7,365,221 discloses monoacylated betulin and dihydrobetuline derivatives, and their use as anti-HIV agents. As discussed in the '221 reference, esterification of betulinic acid (1) with certain substituted acyl groups, such as 3',3'-dimethylglutaryl and 3',3'-dimethylsuccinyl groups produced derivatives having enhanced activity (Kashiwada, Y., et al., J. Med. Chem. 39:1016-1017 (1996)). Acylated betulinic acid and dihydrobetulinic acid derivatives that are potent anti-HIV agents are also described in U.S. Pat. No. 5,679,828. Esterification of the hydroxyl in the 3 carbon of betulin with succinic acid also produced a compound capable of inhibiting HIV-1 activity (Pokrovskii, A. G., et al., "Synthesis of derivatives of plant triterpenes and study of their antiviral and immunostimulating activity," Khimiya y Interesakh Ustoichivogo Razvitiya, Vol. 9, No. 3, pp. 485-491 (2001) (English abstract).

Other references to the use of treating HIV infection with compounds derived from betulinic acid include US 2005/0239748 and US 2008/0207573, as well as WO2006/053255, WO2009/100532 and WO2011/007230.

One HIV maturation compound that has been in development has been identified as Bevirimat or PA-457, with the chemical formula of $C_{36}H_{56}O_6$ and the IUPAC name of 3β-(3-carboxy-3-methyl-butanoyloxy) lup-20(29)-en-28-oic acid.

Reference is also made herein to the applications by Bristol-Myers Squibb entitled "MODIFIED C-3 BETULINIC ACID DERIVATIVES AS HIV MATURATION INHIBITORS" U.S. Ser. No. 13/151,706 filed on Jun. 2, 2011 (now U.S. Pat. No. 8,754,068) and "C-28 AMIDES OF MODIFIED C-3 BETULINIC ACID DERIVATIVES AS HIV MATURATION INHIBITORS" U.S. Ser. No. 13/151,722, filed on Jun. 2, 2011 (now U.S. Pat. No. 8,802,661).

Reference is also made to the application entitled "C-28 AMINES OF C-3 MODIFIED BETULINIC ACID DERIVATIVES AS HIV MATURATION INHIBITORS" U.S. Ser. No. 13/359,680, filed on Jan. 27, 2012 (now U.S. Pat. No. 8,748,415). In addition, reference is made to the application entitled "C-17 AND C-3 MODIFIED TRITERPENOIDS WITH HIV MATURATION INHIBITORY ACTIVITY" U.S. Ser. No. 13/359,727 filed on Jan. 27, 2012 (now U.S. Pat. No. 8,846,647). Further reference is also made to the application "C-3 CYCLOALKENYL TRITERPENOIDS WITH HIV MATURATION INHIBITORY ACTIVITY" filed U.S. Ser. No. 13/760,726 on Feb. 6, 2013 (now U.S. Pat. No. 8,906,889), as well as to the application entitled "TRITERPENOIDS WITH HIV MATURATION INHIBITORY ACTIVITY" U.S. Ser. No. 14/682,179 filed on Apr. 9, 2015.

What is now needed in the art are new compounds which are useful as HIV maturation inhibitors, as well as new pharmaceutical compositions containing these compounds.

SUMMARY OF THE INVENTION

The present invention provides compounds of Formula I below, including pharmaceutically acceptable salts thereof, their pharmaceutical formulations, and their use in patients suffering from or susceptible to a virus such as HIV. The compounds of Formula I are effective antiviral agents, particularly as inhibitors of HIV. They are useful for the treatment of HIV and AIDS.

One embodiment of the present invention is directed to a compound, including pharmaceutically acceptable salts thereof, which is selected from a compound of Formula I:

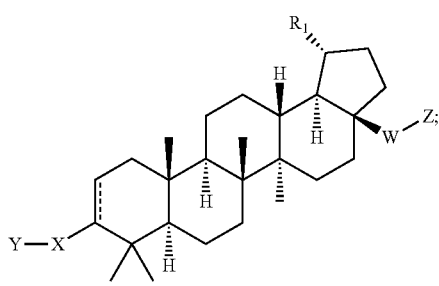

Formula I wherein $R_1$ is isopropenyl or isopropyl;

X is selected from the group of phenyl, heteroaryl, $C_{4-8}$ cycloalkyl, $C_{4-8}$ cycloalkenyl, $C_{4-9}$ spirocycloalkyl, $C_{4-9}$ spirocycloalkenyl, $C_{4-8}$ oxacycloalkyl, $C_{6-8}$ dioxacycloalkenyl, $C_{6-9}$ oxaspirocycloalkyl and $C_{6-9}$ oxaspirocycloalkenyl ring;

wherein X is substituted with A, wherein A is at least one member selected from the group of —H, -halo, -hydroxyl, —$C_{1-6}$ alkyl, —$C_{1-6}$ alkoxy, —$C_{1-6}$haloalkyl, —CN, —$COOR_2$, —$CONR_2R_2$, —$NR_8R_9$, and —$C_{1-6}$ alkyl-Q;

Q is selected from the group of aryl, heteroaryl, substituted heteroaryl, —$OR_2$, —$COOR_3$, —$NR_2R_2$, —$SO_2R_7$, —$CONHSO_2R_3$, and —$CONHSO_2NR_2R_2$;

$R_2$ is —H, —$C_{1-6}$ alkyl, -alkylsubstituted $C_{1-6}$ alkyl or benzyl;

Y is selected from the group of —$COOR_2$, —C(O) $NR_2SO_2R_3$, —C(O)NHSO$_2$NR$_2$R$_2$, —NR$_2$SO$_2$R$_2$, —SO$_2$NR$_2$R$_2$, —$C_{3-6}$ cycloalkyl-$COOR_2$, —$C_{2-6}$ alkenyl-$COOR_2$, —$C_{2-6}$ alkynyl-$COOR_2$, —$C_{1-6}$ alkyl-$COOR_2$, -alkylsubstituted-$C_{1-6}$ alkyl-$COOR_2$, —$CF_2$— $COOR_2$, —$NHC(O)(CH_2)_n$—$COOR_2$, —$SO_2NR_2C(O) R_2$, -tetrazole, and —$CONHOH$, wherein n=1-6;

W is absent or is

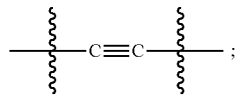

Z is a heteroaryl group, wherein Z can be substituted with —H, —$C_{1-6}$ alkyl, —$C_{1-6}$ substituted alkyl, —$C_{1-6}$ alkyl-$Q_1$, —$CONR_{10}R_{11}$, and —$COOR_2$;

$Q_1$ is selected from the group of heteroaryl, substituted heteroaryl, halogen, —$CF_3$, —$OR_2$, —$COOR_2$, —$NR_4R_5$, —$CONR_{10}R_{11}$ and —$SO_2R_7$;

$R_3$ is —H, —$C_{1-6}$ alkyl, -alkylsubstituted $C_{1-6}$ alkyl or benzyl;

$R_4$ is selected from the group of —H, —$C_{1-6}$ alkyl, —$C_{1-6}$ alkyl-$C(OR_3)_2$—$C_{3-6}$ cycloalkyl, —$C_{1-6}$ substituted alkyl, —$C_{1-6}$ alkyl-$C_{3-6}$ cycloalkyl, —$C_{1-6}$ alkyl-$Q_1$, —$C_{1-6}$ alkyl-$C_{3-6}$ cycloalkyl-$Q_1$, aryl, heteroaryl, substituted heteroaryl, —$COR_6$, —$COCOR_6$, —$SO_2R_7$, and —$SO_2NR_2R_2$;

$R_5$ is selected from the group of —H, —$C_{1-6}$ alkyl, —$C_{3-6}$ cycloalkyl, —$C_{1-6}$ alkylsubstituted alkyl, —$C_{1-6}$ alkyl-$NR_8R_9$, —$COR_{10}$, —$COR_6$, —$COCOR_6$, —$SO_2R_7$ and —$SO_2NR_2R_2$;

or $R_4$ and $R_5$ are taken together with the adjacent N to form a cycle selected from the group of:

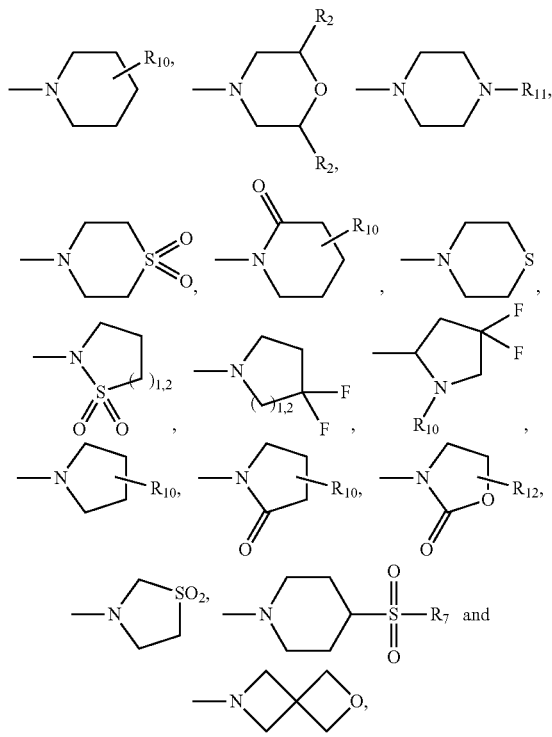

with the proviso that only one of $R_4$ or $R_5$ can be selected from the group of —$COR_6$, —$COCOR_6$, —$SO_2R_7$ and —$SO_2NR_2R_2$;

$R_6$ is selected from the group of —H, —$C_{1-6}$ alkyl, —$C_{1-6}$ alkyl-substitutedalkyl, —$C_{3-6}$ cycloalkyl, —$C_{3-6}$ substitutedcycloalkyl-$Q_2$, —$C_{1-6}$ alkyl-$Q_2$, —$C_{1-6}$ alkyl-substitutedalkyl-$Q_2$, —$C_{3-6}$ cycloalkyl-$Q_2$, aryl-$Q_2$, —$NR_2R_2$, and —$OR_3$;

$Q_2$ is selected from the group of aryl, heteroaryl, substituted heteroaryl, —$OR_2$, —$COOR_2$, —$NR_8R_9$, $SO_2R_7$, —$CONHSO_2R_3$, and —$CONHSO_2NR_2R_2$;

$R_7$ is selected from the group of —H, —$C_{1-6}$ alkyl, —$C_{1-6}$ substituted alkyl, —$C_{3-6}$ cycloalkyl, —$CF_3$, aryl, and heteroaryl;

$R_8$ and $R_9$ are independently selected from the group of —H, —$C_{1-6}$ alkyl, —$C_{1-6}$ substituted alkyl, aryl, heteroaryl, substituted aryl, substituted heteroaryl, —$C_{1-6}$ alkyl-$Q_2$, and —$COOR_3$, or $R_8$ and $R_9$ are taken together with the adjacent N to form a cycle selected from the group of:

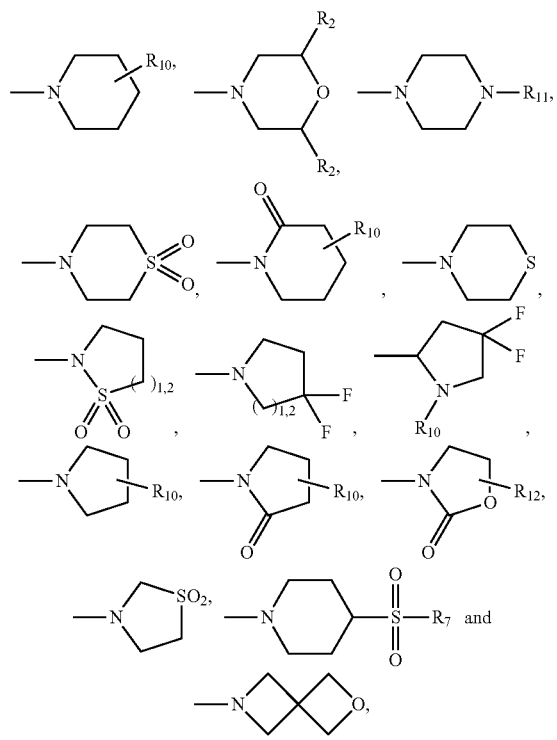

with the proviso that only one of $R_8$ or $R_9$ can be —$COOR_3$;

$R_{10}$ is selected from the group of —H, —$C_{1-6}$ alkyl, —$NR_2R_2$, and —$COOR_3$;

$R_{11}$ is selected from the group of —H, —$C_{1-6}$ alkyl, —$C_{1-6}$ alkyl-OH; —$C_{1-6}$ alkyl, —$C_{1-6}$ substituted alkyl, —$C_{3-6}$ cycloalkyl, —$COR_7$, —$COONR_2R_2$, —$SOR_7$, and —$SONR_2R_2$; and $R_{12}$ is selected from the group of —H, —$C_{1-6}$ alkyl, —$COOR_3$, and aryl.

In a further embodiment, there is provided a method for treating mammals infected with a virus, especially wherein said virus is HIV, comprising administering to said mammal an antiviral effective amount of a compound which is selected from the group of compounds of Formula I, and one or more pharmaceutically acceptable carriers, excipients or diluents. Optionally, the compound of Formula I can be administered in combination with an antiviral effective amount of another AIDS treatment agent selected from the group consisting of: (a) an AIDS antiviral agent; (b) an anti-infective agent; (c) an immunomodulator; and (d) other HIV entry inhibitors.

Another embodiment of the present invention is a pharmaceutical composition comprising one or more compounds of Formula I, and one or more pharmaceutically acceptable carriers, excipients, and/or diluents; and optionally in combination with another AIDS treatment agent selected from the group consisting of: (a) an AIDS antiviral agent; (b) an anti-infective agent; (c) an immunomodulator; and (d) other HIV entry inhibitors.

In another embodiment of the invention there is provided one or more methods for making the compounds of Formula I herein.

Also provided herein are intermediate compounds useful in making the compounds of Formula I herein.

The present invention is directed to these, as well as other important ends, hereinafter described.

DETAILED DESCRIPTION OF THE EMBODIMENTS

As used herein, the singular forms "a", "an", and "the" include plural reference unless the context clearly dictates otherwise.

Since the compounds of the present invention may possess asymmetric centers and therefore occur as mixtures of diastereomers, the present disclosure includes the individual diastereoisomeric forms of the compounds of Formula I in addition to the mixtures thereof.

Definitions

Unless otherwise specifically set forth elsewhere in the application, one or more of the following terms may be used herein, and shall have the following meanings:

"H" refers to hydrogen, including its isotopes, such as deuterium.

The term "$C_{1-6}$ alkyl" as used herein and in the claims (unless specified otherwise) mean straight or branched chain alkyl groups such as methyl, ethyl, propyl, isopropyl, butyl, isobutyl, t-butyl, amyl, hexyl and the like.

"$C_1$-$C_4$ fluoroalkyl" refers to F-substituted $C_1$-$C_4$ alkyl wherein at least one H atom is substituted with F atom, and each H atom can be independently substituted by F atom;

"Halogen" or "halo" refers to chlorine, bromine, iodine or fluorine.

An "aryl" or "Ar" group refers to an all carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or unsubstituted. When substituted, the substituent group(s) are preferably one or more selected from alkyl, cycloalkyl, aryl, heteroaryl, heteroalicyclic, hydroxy, alkoxy, aryloxy, heteroaryloxy, heteroalicycloxy, thiohydroxy, thioaryloxy, thioheteroaryloxy, thioheteroalicycloxy, cyano, halogen, nitro, carbonyl, O-carbamyl, N-carbamyl, C-amido, N-amido, C-carboxy, O-carboxy, sulfinyl, sulfonyl, sulfonamido, trihalomethyl, ureido, amino and —$NR^xR^y$, wherein $R^x$ and $R^y$ are independently selected from the group consisting of hydrogen, alkyl, cycloalkyl, aryl, carbonyl, C-carboxy, sulfonyl, trihalomethyl, and, combined, a five- or six-member heteroalicyclic ring.

A "heteroaryl" group refers to a monocyclic or fused ring (i.e., rings which share an adjacent pair of atoms) group having in the ring(s) one or more atoms selected from the group consisting of nitrogen, oxygen and sulfur and, in addition, having a completely conjugated pi-electron system. Unless otherwise indicated, the heteroaryl group may be attached at either a carbon or nitrogen atom within the heteroaryl group. It should be noted that the term heteroaryl is intended to encompass an N-oxide of the parent heteroaryl if such an N-oxide is chemically feasible as is known in the art. Examples, without limitation, of heteroaryl groups are furyl, thienyl, benzothienyl, thiazolyl, imidazolyl, oxazolyl, oxadiazolyl, thiadiazolyl, benzothiazolyl, triazolyl, tetrazolyl, isoxazolyl, isothiazolyl, pyrrolyl, pyranyl, tetrahydropyranyl, pyrazolyl, pyridyl, pyrimidinyl, quinolinyl, isoquinolinyl, purinyl, carbazolyl, benzoxazolyl, benzimidazolyl, indolyl, isoindolyl, pyrazinyl. diazinyl, pyrazine, triazinyl, tetrazinyl, and tetrazolyl. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thioalkoxy, thiohydroxy, thioaryloxy, thioheteroaryloxy, thioheteroalicycloxy, cyano, halogen, nitro, carbonyl, O-carbamyl, N-carbamyl, C-amido, N-amido, C-carboxy, O-carboxy, sulfinyl, sulfonyl, sulfonamido, trihalomethyl, ureido, amino, and —NR$^x$R$^y$, wherein R$^x$ and R$^y$ are as defined above.

A "heteroalicyclic" group refers to a monocyclic or fused ring group having in the ring(s) one or more atoms selected from the group consisting of nitrogen, oxygen and sulfur. Rings are selected from those which provide stable arrangements of bonds and are not intended to encompass systems which would not exist. The rings may also have one or more double bonds. However, the rings do not have a completely conjugated pi-electron system. Examples, without limitation, of heteroalicyclic groups are azetidinyl, piperidyl, piperazinyl, imidazolinyl, thiazolidinyl, 3-pyrrolidin-1-yl, morpholinyl, thiomorpholinyl and its S oxides and tetrahydropyranyl. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halogen, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, silyl, guanyl, guanidino, ureido, phosphonyl, amino and —NR$^x$R$^y$, wherein R$^x$ and R$^y$ are as defined above.

An "alkyl" group refers to a saturated aliphatic hydrocarbon including straight chain and branched chain groups. Preferably, the alkyl group has 1 to 20 carbon atoms (whenever a numerical range; e.g., "1-20", is stated herein, it means that the group, in this case the alkyl group may contain 1 carbon atom, 2 carbon atoms, 3 carbon atoms, etc. up to and including 20 carbon atoms). More preferably, it is a medium size alkyl having 1 to 10 carbon atoms. Most preferably, it is a lower alkyl having 1 to 4 carbon atoms. The alkyl group may be substituted or unsubstituted. When substituted, the substituent group(s) is preferably one or more individually selected from trihaloalkyl, cycloalkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halo, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, and combined, a five- or six-member heteroalicyclic ring.

A "cycloalkyl" group refers to an all-carbon monocyclic or fused ring (i.e., rings which share and adjacent pair of carbon atoms) group wherein one or more rings does not have a completely conjugated pi-electron system. Examples, without limitation, of cycloalkyl groups are cyclopropane, cyclobutane, cyclopentane, cyclopentene, cyclohexane, cyclohexene, cycloheptane, cycloheptene and adamantane. A cycloalkyl group may be substituted or unsubstituted. When substituted, the substituent group(s) is preferably one or more individually selected from alkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halo, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, silyl, amidino, guanidino, ureido, phosphonyl, amino and —NR$^x$R$^y$ with R$^x$ and R$^y$ as defined above.

An "alkenyl" group refers to an alkyl group, as defined herein, having at least two carbon atoms and at least one carbon-carbon double bond.

An "alkynyl" group refers to an alkyl group, as defined herein, having at least two carbon atoms and at least one carbon-carbon triple bond.

A "hydroxy" group refers to an —OH group.

An "alkoxy" group refers to both an —O-alkyl and an —O-cycloalkyl group as defined herein.

An "aryloxy" group refers to both an —O-aryl and an —O-heteroaryl group, as defined herein.

A "heteroaryloxy" group refers to a heteroaryl-O-group with heteroaryl as defined herein.

A "heteroalicycloxy" group refers to a heteroalicyclic-O-group with heteroalicyclic as defined herein.

A "thiohydroxy" group refers to an —SH group.

A "thioalkoxy" group refers to both an S-alkyl and an —S-cycloalkyl group, as defined herein.

A "thioaryloxy" group refers to both an —S-aryl and an —S-heteroaryl group, as defined herein.

A "thioheteroaryloxy" group refers to a heteroaryl-S-group with heteroaryl as defined herein.

A "thioheteroalicycloxy" group refers to a heteroalicyclic-S-group with heteroalicyclic as defined herein.

A "carbonyl" group refers to a —C(=O)—R" group, where R" is selected from the group consisting of hydrogen, alkyl, alkenyl, alkynyl, cycloalkyl, aryl, heteroaryl (bonded through a ring carbon) and heteroalicyclic (bonded through a ring carbon), as each is defined herein.

An "aldehyde" group refers to a carbonyl group where R" is hydrogen.

A "thiocarbonyl" group refers to a —C(=S)—R" group, with R" as defined herein.

A "keto" group refers to a —CC(=O)C-group wherein the carbon on either or both sides of the C=O may be alkyl, cycloalkyl, aryl or a carbon of a heteroaryl or heteroalicyclic group.

A "trihalomethanecarbonyl" group refers to a Z$_3$CC(=O)-group with said Z being a halogen.

A "C-carboxy" group refers to a —C(=O)O—R" groups, with R" as defined herein.

An "O-carboxy" group refers to a R"C(=O)O-group, with R" as defined herein.

A "carboxylic acid" group refers to a C-carboxy group in which R" is hydrogen.

A "trihalomethyl" group refers to a —CZ$_3$, group wherein Z is a halogen group as defined herein.

A "trihalomethanesulfonyl" group refers to an Z$_3$CS(=O) 2-groups with Z as defined above.

A "trihalomethanesulfonamido" group refers to a $Z_3CS(=O)_2NR^x$-group with Z as defined above and $R^x$ being H or $(C_{1-6})$alkyl.

A "sulfinyl" group refers to a —S(=O)—R" group, with R" being $(C_{1-6})$alkyl.

A "sulfonyl" group refers to a —S(=O)$_2$R" group with R" being $(C_{1-6})$alkyl.

A "S-sulfonamido" group refers to a —S(=O)$_2$NR$^x$R$^y$, with R$^X$ and R$^Y$ independently being H or $(C_{1-6})$alkyl.

A "N-sulfonamido" group refers to a R"S(=O)$_2$NR$_x$-group, with R$_x$ being H or $(C_{1-6})$alkyl.

A "O-carbamyl" group refers to a —OC(=O)NR$^x$R$^y$ group, with R$^X$ and R$^Y$ independently being H or $(C_{1-6})$alkyl.

A "N-carbamyl" group refers to a R$^x$OC(=O)NR$^y$ group, with R$^x$ and R$^y$ independently being H or $(C_{1-6})$alkyl.

A "O-thiocarbamyl" group refers to a —OC(=S)NR$^x$R$^y$ group, with R$^x$ and R$^y$ independently being H or $(C_{1-6})$alkyl.

A "N-thiocarbamyl" group refers to a R$^x$OC(=S)NR$^y$-group, with R$^x$ and R$^y$ independently being H or $(C_{1-6})$alkyl.

An "amino" group refers to an —NH$_2$ group.

A "C-amido" group refers to a —C(=O)NR$^x$R$^y$ group, with R$^x$ and R$^y$ independently being H or $(C_{1-6})$alkyl.

A "C-thioamido" group refers to a —C(=S)NR$^x$R$^y$ group, with R$^x$ and R$^y$ independently being H or $(C_{1-6})$alkyl.

A "N-amido" group refers to a R$^x$C(=O)NR$^y$-group, with R$^x$ and R$^y$ independently being H or $(C_{1-6})$alkyl.

An "ureido" group refers to a —NR$^x$C(=O)NR$^y$R$^{y2}$ group, with R$^x$, R$^y$, and R$^{y2}$ independently being H or $(C_{1-6})$alkyl.

A "guanidino" group refers to a —R$^x$NC(=N)NR$^y$R$^{y2}$ group, with R$^x$, R$^y$, and R$^{y2}$ independently being H or $(C_{1-6})$alkyl.

A "amidino" group refers to a R$^x$R$^y$NC(=N)-group, with R$^x$ and R$^y$ independently being H or $(C_{1-6})$alkyl.

A "cyano" group refers to a —CN group.

A "silyl" group refers to a —Si(R")$_3$, with R" being $(C_{1-6})$alkyl or phenyl.

A "phosphonyl" group refers to a P(=O)(OR$^x$)$_2$ with R$^x$ being $(C_{1-6})$alkyl.

A "hydrazino" group refers to a —NR$^x$NR$^y$R$^{y2}$ group, with R$^x$, R$^y$, and R$^{y2}$ independently being H or $(C_{1-6})$alkyl.

A "4, 5, or 6 membered ring cyclic N-lactam" group refers to

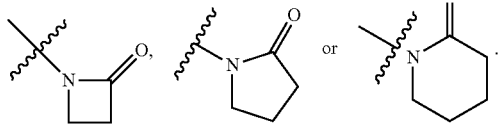

A "spiro" group is a bicyclic organic group with rings connected through just one atom. The rings can be different in nature or identical. The connecting atom is also called the spiroatom, most often a quaternary carbon ("spiro carbon").

An "oxospiro" or "oxaspiro" group is a spiro group having an oxygen contained within the bicyclic ring structure. A "dioxospiro" or "dioxaspiro" group has two oxygens within the bicyclic ring structure.

Any two adjacent R groups may combine to form an additional aryl, cycloalkyl, heteroaryl or heterocyclic ring fused to the ring initially bearing those R groups.

It is known in the art that nitrogen atoms in heteroaryl systems can be "participating in a heteroaryl ring double bond", and this refers to the form of double bonds in the two tautomeric structures which comprise five-member ring heteroaryl groups. This dictates whether nitrogens can be substituted as well understood by chemists in the art. The disclosure and claims of the present disclosure are based on the known general principles of chemical bonding. It is understood that the claims do not encompass structures known to be unstable or not able to exist based on the literature.

Pharmaceutically acceptable salts and prodrugs of compounds disclosed herein are within the scope of the invention. The term "pharmaceutically acceptable salt" as used herein and in the claims is intended to include nontoxic base addition salts. Suitable salts include those derived from organic and inorganic acids such as, without limitation, hydrochloric acid, hydrobromic acid, phosphoric acid, sulfuric acid, methanesulfonic acid, acetic acid, tartaric acid, lactic acid, sulfinic acid, citric acid, maleic acid, fumaric acid, sorbic acid, aconitic acid, salicylic acid, phthalic acid, and the like. The term "pharmaceutically acceptable salt" as used herein is also intended to include salts of acidic groups, such as a carboxylate, with such counterions as ammonium, alkali metal salts, particularly sodium or potassium, alkaline earth metal salts, particularly calcium or magnesium, and salts with suitable organic bases such as lower alkylamines (methylamine, ethylamine, cyclohexylamine, and the like) or with substituted lower alkylamines (e.g. hydroxyl-substituted alkylamines such as diethanolamine, triethanolamine or tris(hydroxymethyl)-aminomethane), or with bases such as piperidine or morpholine.

As stated above, the compounds of the invention also include "prodrugs". The term "prodrug" as used herein encompasses both the term "prodrug esters" and the term "prodrug ethers".

As set forth above, the invention is directed to a compound, including pharmaceutically acceptable salts thereof, which is selected from a compound of Formula I:

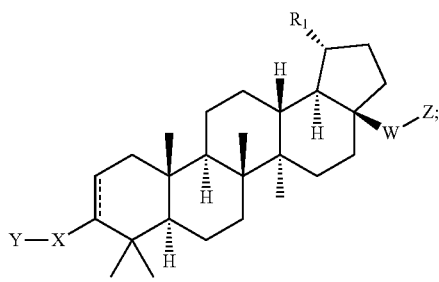

Formula I wherein R$_1$ is isopropenyl or isopropyl;

X is selected from the group of phenyl, heteroaryl, C$_{4-8}$ cycloalkyl, C$_{4-8}$ cycloalkenyl, C$_{4-9}$ spirocycloalkyl, C$_{4-9}$ spirocycloalkenyl, C$_{4-8}$ oxacycloalkyl, C$_{6-8}$ dioxacycloalkenyl, C$_{6-9}$ oxaspirocycloalkyl and C$_{6-9}$ oxaspirocycloalkenyl ring;

wherein X is substituted with A, wherein A is at least one member selected from the group of —H, -halo, -hydroxyl, —C$_{1-6}$ alkyl, —C$_{1-6}$ alkoxy, —C$_{1-6}$haloalkyl, —CN, —COOR$_2$, —CONR$_2$R$_2$, —NR$_8$R$_9$, and —C$_{1-6}$ alkyl-Q;

Q is selected from the group of aryl, heteroaryl, substituted heteroaryl, —OR$_2$, —COOR$_3$, —NR$_2$R$_2$, —SO$_2$R$_7$, —CONHSO$_2$R$_3$, and —CONHSO$_2$NR$_2$R$_2$;

R$_2$ is —H, —C$_{1-6}$ alkyl, -alkylsubstituted C$_{1-6}$ alkyl or benzyl;

Y is selected from the group of —COOR$_2$, —C(O)NR$_2$SO$_2$R$_3$, —C(O)NHSO$_2$NR$_2$R$_2$, —NR$_2$SO$_2$R$_2$, —SO$_2$NR$_2$R$_2$, —C$_{3-6}$ cycloalkyl-COOR$_2$, —C$_{2-6}$ alkenyl-COOR$_2$, —C$_{2-6}$ alkynyl-COOR$_2$, —C$_{1-6}$ alkyl-COOR$_2$, -alkylsubstituted-C$_{1-6}$ alkyl-COOR$_2$, —CF$_2$—COOR$_2$, —NHC(O)(CH$_2$)$_n$—COOR$_2$, —SO$_2$NR$_2$C(O)R$_2$, -tetrazole, and —CONHOH, wherein n=1-6;

W is absent or is

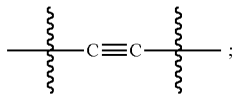 [SMILES: *C#C*]

Z is a heteroaryl group, wherein Z can be substituted with —H, —C$_{1-6}$ alkyl, —C$_{1-6}$ substituted alkyl, —C$_{1-6}$ alkyl-Q$_1$, —CONR$_{10}$R$_{11}$, and —COOR$_2$;

Q$_1$ is selected from the group of heteroaryl, substituted heteroaryl, halogen, —CF$_3$, —OR$_2$, —COOR$_2$, —NR$_4$R$_5$, —CONR$_{10}$R$_{11}$ and —SO$_2$R$_7$;

R$_3$ is —H, —C$_{1-6}$ alkyl, -alkylsubstituted C$_{1-6}$ alkyl or benzyl;

R$_4$ is selected from the group of —H, —C$_{1-6}$ alkyl, —C$_{1-6}$ alkyl-C(OR$_3$)$_2$—C$_{3-6}$ cycloalkyl, —C$_{1-6}$ substituted alkyl, —C$_{1-6}$ alkyl-C$_{3-6}$ cycloalkyl, —C$_{1-6}$ alkyl-Q$_1$, —C$_{1-6}$ alkyl-C$_{3-6}$ cycloalkyl-Q$_1$, aryl, heteroaryl, substituted heteroaryl, —COR$_6$, —COCOR$_6$, —SO$_2$R$_7$, and —SO$_2$NR$_2$R$_2$;

R$_5$ is selected from the group of —H, —C$_{1-6}$ alkyl, —C$_{3-6}$ cycloalkyl, —C$_{1-6}$ alkylsubstituted alkyl, —C$_{1-6}$ alkyl-NR$_8$R$_9$, —COR$_{10}$, —COR$_6$, —COCOR$_6$, —SO$_2$R$_7$ and —SO$_2$NR$_2$R$_2$;

or R$_4$ and R$_5$ are taken together with the adjacent N to form a cycle selected from the group of:

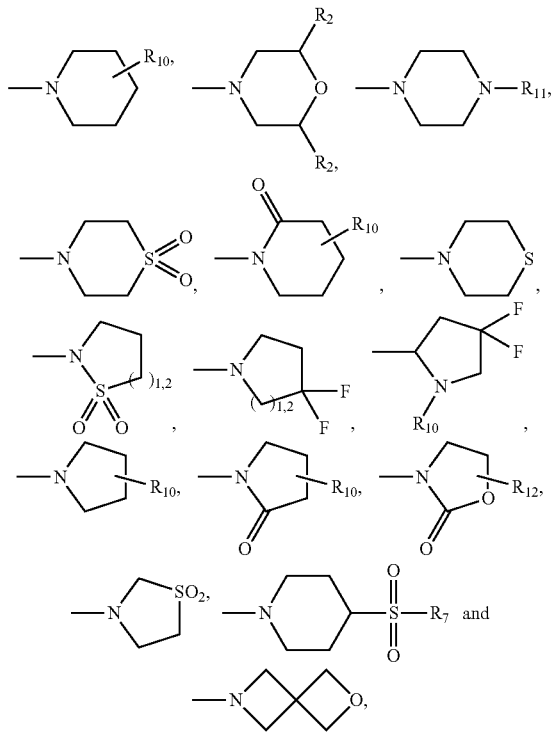

with the proviso that only one of R$_4$ or R$_5$ can be selected from the group of —COR$_6$, —COCOR$_6$, —SO$_2$R$_7$ and —SO$_2$NR$_2$R$_2$;

R$_6$ is selected from the group of —H, —C$_{1-6}$ alkyl, —C$_{1-6}$ alkyl-substitutedalkyl, —C$_{3-6}$ cycloalskyl, —C$_{3-6}$ substitutedcycloalkyl-Q$_2$, —C$_{1-6}$ alkyl-Q$_2$, —C$_{1-6}$ alkyl-substitutedalkyl-Q$_2$, —C$_{3-6}$ cycloalkyl-Q$_2$, aryl-Q$_2$, —NR$_2$R$_2$, and —OR$_3$;

Q$_2$ is selected from the group of aryl, heteroaryl, substituted heteroaryl, —OR$_2$, —COOR$_2$, —NR$_8$R$_9$, SO$_2$R$_7$, —CONHSO$_2$R$_3$, and —CONHSO$_2$NR$_2$R$_2$;

R$_7$ is selected from the group of —H, —C$_{1-6}$ alkyl, —C$_{1-6}$ substituted alkyl, —C$_{3-6}$ cycloalkyl, —CF$_3$, aryl, and heteroaryl;

R$_8$ and R$_9$ are independently selected from the group of —H, —C$_{1-6}$ alkyl, —C$_{1-6}$ substituted alkyl, aryl, heteroaryl, substituted aryl, substituted heteroaryl, —C$_{1-6}$ alkyl-Q$_2$, and —COOR$_3$, or R$_8$ and R$_9$ are taken together with the adjacent N to form a cycle selected from the group of:

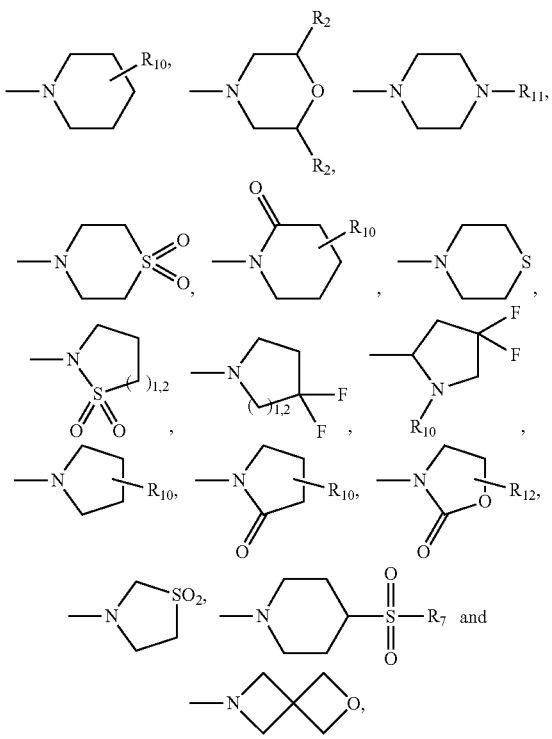

with the proviso that only one of R$_8$ or R$_9$ can be —COOR$_3$;

R$_{10}$ is selected from the group of —H, —C$_{1-6}$ alkyl, —NR$_2$R$_2$, and —COOR$_3$;

R$_{11}$ is selected from the group of —H, —C$_{1-6}$ alkyl, —C$_{1-6}$ alkyl-OH; —C$_{1-6}$ alkyl, —C$_{1-6}$ substituted alkyl, —C$_{3-6}$ cycloalkyl, —COR$_7$, —COONR$_2$R$_2$, —SOR$_7$, and —SONR$_2$R$_2$; and R$_{12}$ is selected from the group of —H, —C$_{1-6}$ alkyl, —COORS, and aryl.

In a preferred embodiment of the invention, X is selected from phenyl.

It is also preferred that Y is —COOH.

It is further preferred that R$_1$ is isopropenyl.

Preferred compounds, including pharmaceutically acceptable salts thereof, as part of the invention include the following:

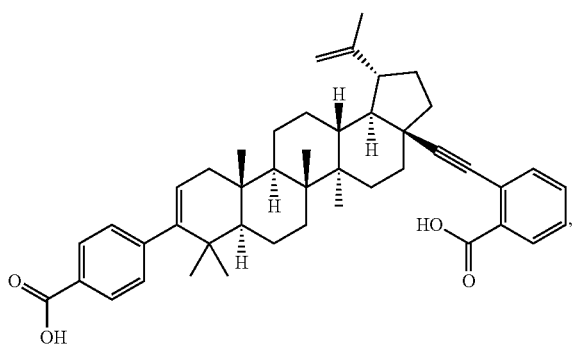

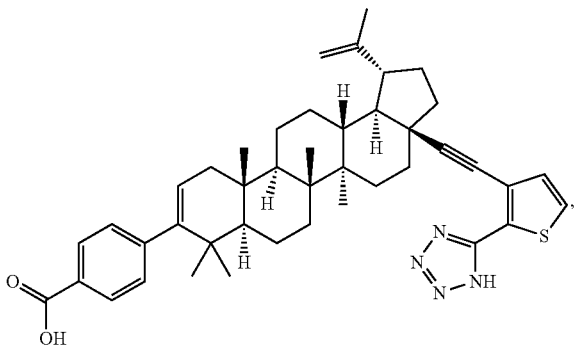

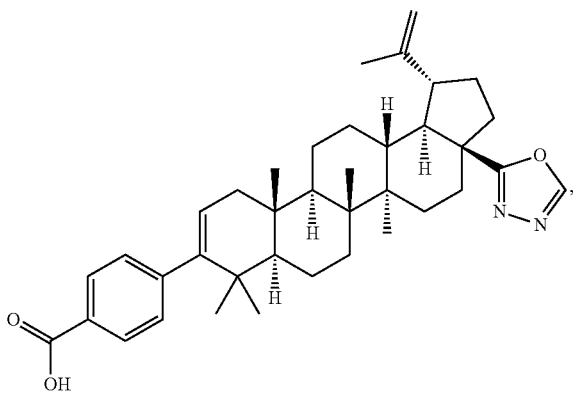

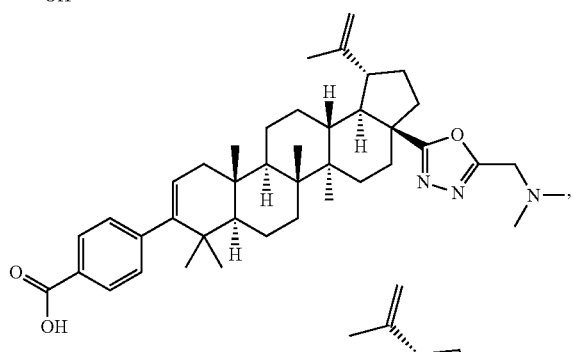

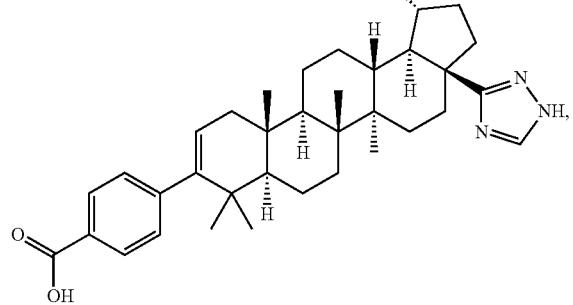

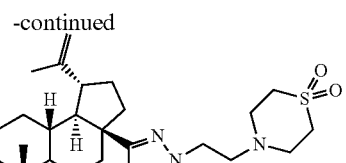

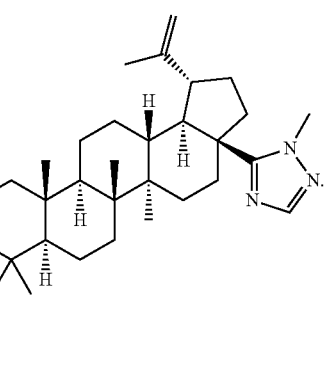

and

The compounds above represent the mixture of diastereoisomers, and the two individual disastereomers. In certain embodiments, one of the specific diastereomers may be particularly preferred.

The compounds of the present invention, according to all the various embodiments described above, may be administered orally, parenterally (including subcutaneous injections, intravenous, intramuscular, intrasternal injection or infusion techniques), by inhalation spray, or rectally, and by other means, in dosage unit formulations containing non-toxic pharmaceutically acceptable carriers, excipients and diluents available to the skilled artisan. One or more adjuvants may also be included.

Thus, in accordance with the present invention, there is further provided a method of treatment, and a pharmaceutical composition, for treating viral infections such as HIV infection and AIDS. The treatment involves administering to a patient in need of such treatment a pharmaceutical composition which contains an antiviral effective amount of one or more of the compounds of Formula I together with one or more pharmaceutically acceptable carriers, excipients or diluents. As used herein, the term "antiviral effective amount" means the total amount of each active component of the composition and method that is sufficient to show a meaningful patient benefit, i.e., inhibiting, ameliorating, or healing of acute conditions characterized by inhibition of HIV infection. When applied to an individual active ingredient, administered alone, the term refers to that ingredient alone. When applied to a combination, the term refers to combined amounts of the active ingredients that result in the therapeutic effect, whether administered in combination, serially or simultaneously. The terms "treat, treating, treatment" as used herein and in the claims means preventing, inhibiting, ameliorating and/or healing diseases and conditions associated with HIV infection.

The pharmaceutical compositions of the invention may be in the form of orally administrable suspensions or tablets; as well as nasal sprays, sterile injectable preparations, for example, as sterile injectable aqueous or oleaginous suspensions or suppositories. Pharmaceutically acceptable carriers, excipients or diluents may be utilized in the pharmaceutical compositions, and are those utilized in the art of pharmaceutical preparations.

When administered orally as a suspension, these compositions are prepared according to techniques typically known in the art of pharmaceutical formulation and may contain microcrystalline cellulose for imparting bulk, alginic acid or sodium alginate as a suspending agent, methylcellulose as a viscosity enhancer, and sweeteners/flavoring agents known in the art. As immediate release tablets, these compositions may contain microcrystalline cellulose, dicalcium phosphate, starch, magnesium stearate and lactose and/or other excipients, binders, extenders, disintegrants, diluents, and lubricants known in the art.

The injectable solutions or suspensions may be formulated according to known art, using suitable non-toxic, parenterally acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

The compounds herein set forth can be administered orally to humans in a dosage range of about 1 to 100 mg/kg body weight in divided doses, usually over an extended period, such as days, weeks, months, or even years. One preferred dosage range is about 1 to 10 mg/kg body weight orally in divided doses. Another preferred dosage range is about 1 to 20 mg/kg body weight in divided doses. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Also contemplated herein are combinations of the compounds of Formula I herein set forth, together with one or more other agents useful in the treatment of AIDS. For example, the compounds of this disclosure may be effectively administered, whether at periods of pre-exposure and/or post-exposure, in combination with effective amounts of the AIDS antivirals, immunomodulators, antiinfectives, or vaccines, such as those in the following non-limiting table:

| Drug Name | Manufacturer | Indication |
|---|---|---|
| ANTIVIRALS | | |
| 097 | Hoechst/Bayer | HIV infection, AIDS, ARC (non-nucleoside reverse transcriptase (RT) inhibitor) |
| Amprenavir 141 W94 GW 141 | Glaxo Wellcome | HIV infection, AIDS, ARC (protease inhibitor) |
| Abacavir (1592U89) GW 1592 | Glaxo Wellcome | HIV infection, AIDS, ARC (RT inhibitor) |
| Acemannan | Carrington Labs (Irving, TX) | ARC |
| Acyclovir | Burroughs Wellcome | HIV infection, AIDS, ARC |
| AD-439 | Tanox Biosystems | HIV infection, AIDS, ARC |
| AD-519 | Tanox Biosystems | HIV infection, AIDS, ARC |
| Adefovir dipivoxil | Gilead Sciences | HIV infection |
| AL-721 | Ethigen (Los Angeles, CA) | ARC, PGL HIV positive, AIDS |
| Alpha Interferon | Glaxo Wellcome | Kaposi's sarcoma, HIV in combination w/Retrovir |
| Ansamycin LM 427 | Adria Laboratories (Dublin, OH) Erbamont (Stamford, CT) | ARC |
| Antibody which Neutralizes pH Labile alpha aberrant Interferon | Advanced Biotherapy Concepts (Rockville, MD) | AIDS, ARC |
| AR177 | Aronex Pharm | HIV infection, AIDS, ARC |
| Beta-fluoro-ddA | Nat'l Cancer Institute | AIDS-associated diseases |
| BMS-234475 (CGP-61755) | Bristol-Myers Squibb/ Novartis | HIV infection, AIDS, ARC (protease inhibitor) |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus Immune globin | MedImmune | CMV retinitis |

-continued

| Drug Name | Manufacturer | Indication |
|---|---|---|
| Cytovene Ganciclovir | Syntex | Sight threatening CMV peripheral CMV retinitis |
| Darunavir | Tibotec-J & J | HIV infection, AIDS, ARC (protease inhibitor) |
| Delaviridine | Pharmacia-Upjohn | HIV infection, AIDS, ARC (RT inhibitor) |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 | AVID (Camden, NJ) | HIV infection, AIDS, ARC (protease inhibitor) |
| Efavirenz (DMP 266, SUSTIVA ®) (−)6-Chloro-4-(S)-cyclopropylethynyl-4(S)-trifluoro-methyl-1,4-dihydro-2H-3,1-benzoxazin-2-one, STOCRINE | Bristol Myers Squibb | HIV infection, AIDS, ARC (non-nucleoside RT inhibitor) |
| EL10 | Elan Corp, PLC (Gainesville, GA) | HIV infection |
| Etravirine | Tibotec/J & J | HIV infection, AIDS, ARC (non-nucleoside reverse transcriptase inhibitor) |
| Famciclovir | Smith Kline | herpes zoster, herpes simplex |
| GS 840 | Gilead | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (RT inhibitor) |
| Novapren | Novaferon Labs, Inc. (Akron, OH) | HIV inhibitor |
| Peptide T Octapeptide Sequence | Peninsula Labs (Belmont, CA) | AIDS |

-continued

| Drug Name | Manufacturer | Indication |
|---|---|---|
| Trisodium Phosphonoformate | Astra Pharm. Products, Inc. | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston, TX) | HIV infection, AIDS, ARC |
| Ritonavir | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxy-Thymidine | Bristol-Myers Squibb | HIV infection, AIDS, ARC |
| Tipranavir | Boehringer Ingelheim | HIV infection, AIDS, ARC (protease inhibitor) |
| Valaciclovir | Glaxo Wellcome | Genital HSV & CMV infections |
| Virazole Ribavirin | Viratek/ICN (Costa Mesa, CA) | asymptomatic HIV positive, LAS, ARC |
| VX-478 | Vertex | HIV infection, AIDS, ARC |
| Zalcitabine | Hoffmann-LaRoche | HIV infection, AIDS, ARC, with AZT |
| Zidovudine; AZT | Glaxo Wellcome | HIV infection, AIDS, ARC, Kaposi's sarcoma, in combination with other therapies |
| Tenofovir disoproxil, fumarate salt (VIREAD ®) | Gilead | HIV infection, AIDS, (reverse transcriptase inhibitor) |
| EMTRIVA ® (Emtricitabine) (FTC) | Gilead | HIV infection, AIDS, (reverse transcriptase inhibitor) |
| COMBIVIR ® | GSK | HIV infection, AIDS, (reverse transcriptase inhibitor) |
| Abacavir succinate (or ZIAGEN ®) | GSK | HIV infection, AIDS, (reverse transcriptase inhibitor) |
| REYATAZ ® (or atazanavir) | Bristol-Myers Squibb | HIV infection AIDs, protease inhibitor |
| FUZEON ® (Enfuvirtide or T-20) | Roche/Trimeris | HIV infection AIDs, viral Fusion inhibitor |
| LEXIVA ® (or Fosamprenavir calcium) | GSK/Vertex | HIV infection AIDs, viral protease inhibitor |
| Selzentry Maraviroc; (UK 427857) | Pfizer | HIV infection AIDs, (CCR5 antagonist, in development) |
| Trizivir ® | GSK | HIV infection AIDs, (three drug combination) |
| Sch-417690 (vicriviroc) | Schering-Plough | HIV infection AIDs, (CCR5 antagonist, in development) |
| TAK-652 | Takeda | HIV infection AIDs, (CCR5 antagonist, in development) |
| GSK 873140 (ONO-4128) | GSK/ONO | HIV infection AIDs, (CCR5 antagonist, in development) |
| Integrase Inhibitor MK-0518 Raltegravir | Merck | HIV infection AIDs |

| Drug Name | Manufacturer | Indication |
|---|---|---|
| TRUVADA ® | Gilead | Combination of Tenofovir disoproxil fumarate salt (VIREAD ®) and EMTRIVA ® (Emtricitabine) |
| Integrase Inhibitor GS917/JTK-303 Elvitegravir | Gilead/Japan Tobacco | HIV Infection AIDs in development |
| Triple drug combination ATRIPLA ® | Gilead/Bristol-Myers Squibb | Combination of Tenofovir disoproxil fumarate salt (VIREAD ®), EMTRIVA ® (Emtricitabine), and SUSTIVA ® (Efavirenz) |
| FESTINAVIR ® 4'-ethynyl-d4T | Oncolys BioPharma BMS | HIV infection AIDs in development |
| CMX-157 Lipid conjugate of nucleotide tenofovir | Chimerix | HIV infection AIDs |
| GSK1349572 Integrase inhibitor dolutegravir | GSK | HIV infection AIDs |
| S/GSK1265744 Integrase inhibitor | GSK | HIV infection AIDs |
| IMMUNOMODULATORS | | |
| AS-101 | Wyeth-Ayerst | AIDS |
| Bropirimine | Pharmacia Upjohn | Advanced AIDS |
| Acemannan | Carrington Labs, Inc. (Irving, TX) | AIDS, ARC |
| CL246,738 | Wyeth Lederle Labs | AIDS, Kaposi's sarcoma |
| FP-21399 | Fuki ImmunoPharm | Blocks HIV fusion with CD4+ cells |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoechst-Roussel Immunex | AIDS |
| Granulocyte Macrophage Colony Stimulating Factor | Schering-Plough | AIDS, combination w/AZT |
| HIV Core Particle Immunostimulant | Rorer | Seropositive HIV |
| IL-2 Interleukin-2 | Cetus | AIDS, in combination w/AZT |
| IL-2 Interleukin-2 | Hoffman-LaRoche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | Pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | Immunotherapeutic |
| rCD4 Recombinant Soluble Human CD4 | Genentech | AIDS, ARC |

-continued

| Drug Name | Manufacturer | Indication |
|---|---|---|
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma AIDS, ARC, in combination w/AZT |
| SK&F106528 Soluble T4 | Smith Kline | HIV infection |
| Thymopentin | Immunobiology Research Institute (Annandale, NJ) | HIV infection |
| Tumor Necrosis Factor; TNF | Genentech | ARC, in combination w/gamma Interferon |
| ANTI-INFECTIVES | | |
| Clindamycin with Primaquine | Pharmacia Upjohn | PCP |
| Fluconazole | Pfizer | Cryptococcal meningitis, candidiasis |
| Pastille Nystatin Pastille | Squibb Corp. | Prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | Antibacterial |
| Trimethoprim/sulfa | | Antibacterial |
| Piritrexim | Burroughs Wellcome | PCP treatment |
| Pentamidine Isethionate for Inhalation | Fisons Corporation | PCP prophylaxis |
| Spiramycin | Rhone-Poulenc | Cryptosporidial diarrhea |
| Intraconazole-R51211 | Janssen-Pharm. | Histoplasmosis; cryptococcal meningitis |
| Trimetrexate | Warner-Lambert | PCP |
| Daunorubicin | NeXstar, Sequus | Kaposi's sarcoma |
| Recombinant Human Erythropoietin | Ortho Pharm. Corp. | Severe anemia assoc. with AZT therapy |
| Recombinant Human Growth Hormone | Serono | AIDS-related wasting, cachexia |
| Megestrol Acetate | Bristol-Myers Squibb | Treatment of anorexia assoc. W/AIDS |
| Testosterone | Alza, Smith Kline | AIDS-related wasting |
| Total Enteral Nutrition | Norwich Eaton Pharmaceuticals | Diarrhea and malabsorption related to AIDS |

Additionally, the compounds of the disclosure herein set forth may be used in combination with HIV entry inhibitors. Examples of such HIV entry inhibitors are discussed in DRUGS OF THE FUTURE 1999, 24(12), pp. 1355-1362; CELL, Vol. 9, pp. 243-246, Oct. 29, 1999; and DRUG DISCOVERY TODAY, Vol. 5, No. 5, May 2000, pp. 183-194 and Inhibitors of the entry of HIV into host cells. Meanwell, Nicholas A.; Kadow, John F., Current Opinion in Drug Discovery & Development (2003), 6(4), 451-461. Specifically the compounds can be utilized in combination with attachment inhibitors, fusion inhibitors, and chemokine receptor antagonists aimed at either the CCR5 or CXCR4 coreceptor. HIV attachment inhibitors are also set forth in U.S. Pat. No. 7,354,924 and U.S. Pat. No. 7,745,625.

It will be understood that the scope of combinations of the compounds of this application with AIDS antivirals, immunomodulators, anti-infectives, HIV entry inhibitors or vaccines is not limited to the list in the above Table but includes, in principle, any combination with any pharmaceutical composition useful for the treatment of AIDS.

Preferred combinations are simultaneous or alternating treatments with a compound of the present disclosure and an inhibitor of HIV protease and/or a non-nucleoside inhibitor of HIV reverse transcriptase. An optional fourth component in the combination is a nucleoside inhibitor of HIV reverse transcriptase, such as AZT, 3TC, ddC or ddI. A preferred inhibitor of HIV protease is REYATAZ® (active ingredient Atazanavir). Typically a dose of 300 to 600 mg is administered once a day. This may be co-administered with a low dose of Ritonavir (50 to 500 mgs). Another preferred inhibitor of HIV protease is KALETRA®. Another useful inhibitor of HIV protease is indinavir, which is the sulfate salt of N-(2(R)-hydroxy-1-(S)-indanyl)-2(R)-phenylmethyl-4-(S)-hydroxy-5-(1-(4-(3-pyridyl-methyl)-2(S)-N'-(t-butylcarboxamido)-piperazinyl))-pentaneamide ethanolate, and is synthesized according to U.S. Pat. No. 5,413,999. Indinavir is generally administered at a dosage of 800 mg three times a day. Other preferred protease inhibitors are nelfinavir and ritonavir. Another preferred inhibitor of HIV protease is saquinavir which is administered in a dosage of 600 or 1200 mg tid. Preferred non-nucleoside inhibitors of HIV reverse transcriptase include efavirenz. These combinations may have unexpected effects on limiting the spread and degree of infection of HIV. Preferred combinations include those with the following (1) indinavir with efavirenz, and, optionally, AZT and/or 3TC and/or ddI and/or ddC; (2) indinavir, and any of AZT and/or ddI and/or ddC and/or 3TC, in particular, indinavir and AZT and 3TC; (3) stavudine and 3TC and/or zidovudine; (4) tenofovir disoproxil fumarate salt and emtricitabine.

In such combinations the compound(s) of the present invention and other active agents may be administered separately or in conjunction. In addition, the administration of one element may be prior to, concurrent to, or subsequent to the administration of other agent(s).

General Chemistry (Methods of Synthesis)

The present invention comprises compounds of Formula I, their pharmaceutical formulations, and their use in patients suffering from or susceptible to HIV infection. The compounds of Formula I also include pharmaceutically acceptable salts thereof. Procedures to construct compounds of Formula I and intermediates useful for their synthesis are described after the Abbreviations.

Abbreviations

One or more of the following abbreviations, most of which are conventional abbreviations well known to those skilled in the art, may be used throughout the description of the disclosure and the examples:
RT=room temperature
BHT=2,6-di-tert-butyl-4-hydroxytoluene
CSA=camphorsulfonic acid
LDA=lithium diisopropylamide
KHMDS=potassium bis(trimethylsilyl)amide
SFC=supercritical fluid chromatography
Quant=quantitative
TBDMS=tert-butyldimethylsilane
PTFE=polytetrafluoroethylene
NMO=4-methylmorpholine-N-oxide
THF=tetrahydrofuran
TLC=thin layer chromatography
DCM=dichloromethane
DCE=dichloroethane
TFA=trifluoroacetic acid
LCMS=liquid chromatography mass spectroscopy
Prep=preparative
HPLC=high performance liquid chromatography
DAST=(diethylamino)sulfur trifluoride
TEA=triethylamine
DIPEA=N,N-diisopropylethylamine
HATU=[O-(7-azabenzotriazol-1-yl)-1,1,3,3-tetramethyluronium hexafluorophosphate]
DCC=N,N'-dicyclohexylcarbodiimide
DMAP=dimethylaminopyridine
TMS=trimethylsilyl
NMR=nuclear magnetic resonance
DPPA=diphenyl phosphoryl azide
AIBN=azobisisobutyronitrile
TBAF=tetrabutylammonium fluoride
DMF=dimethylformamide
TBTU=O-(benzotriazol-1-yl)-N,N,N',N'-tetramethyluronium tetrafluoroborate
Min(s)=minute(s)
h=hour(s)
sat.=saturated
TEA=triethylamine
EtOAc=ethyl acetate
TFA=trifluoroacetic acid
PCC=pyridinium chlorochromate
TLC=thin layer chromatography
Tf$_2$NPh=(trifluoromethylsulfonyl)methanesulfonamide
dioxane=1,4-dioxane
PG=protective group
atm=atmosphere(s)
mol=mole(s)
mmol=milimole(s)
mg=milligram(s)
μg=microgram(s)
μl=microliter(s)
μm=micrometer(s)
mm=millimeter(s)
Rpm=revolutions per minute
SM=starting material
TLC=thin layer chromatography
AP=area percentage
Equiv.=equivalent(s)
DMP=Dess-Martin periodinane
TMSCl=trimethylsilyl chloride
TBSCl=tert-Butyldimethylsilyl chloride
TBSOTf=trimethylsilyl trifluoromethanesulfonate
PhMe=toluene
PhNTf$_2$=N-Phenyl-bis(trifluoromethanesulfonimide)
S-Phos=2-Dicyclohexylphosphino-2',6'-dimethoxybiphenyl
TFDO=methyl(trifluoromethyl)dioxirane
TEMPO=2,2,6,6-tetramethylpiperidinyloxy
DI=deionized water The terms "C-3" and "C-28" refer to certain positions of a triterpene core as numbered in accordance with IUPAC rules (positions depicted below with respect to an illustrative triterpene: betulin):

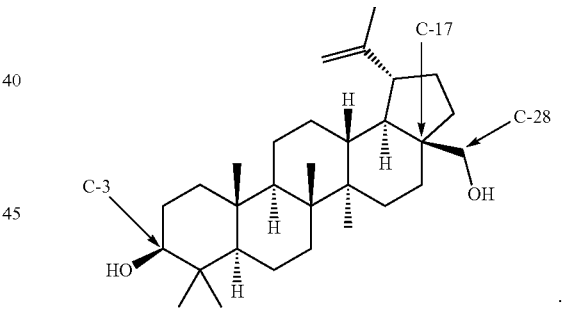

The same numbering is maintained when referring to the compound series in schemes and general descriptions of methods.

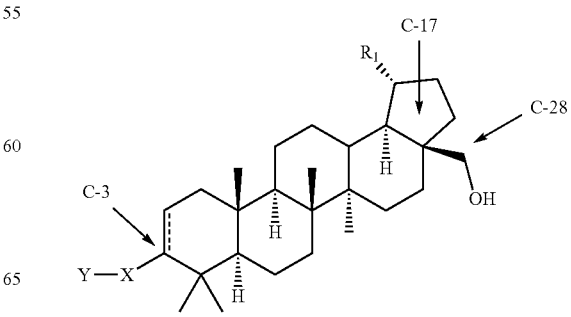

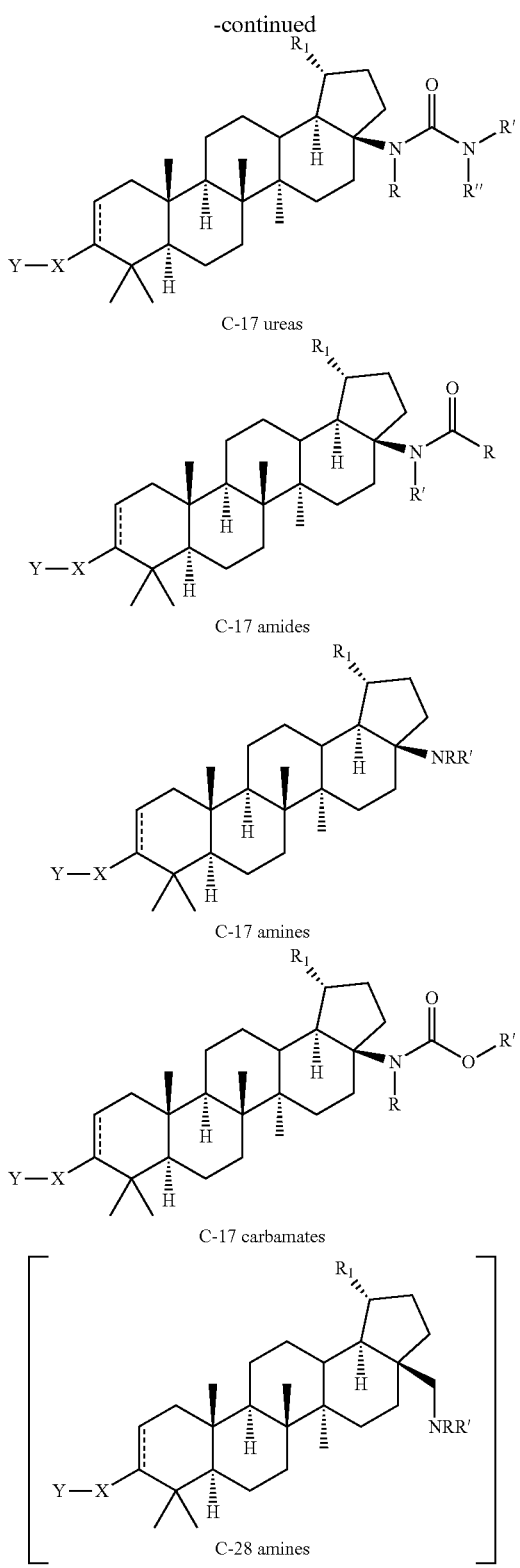

C-17 ureas

C-17 amides

C-17 amines

C-17 carbamates

C-28 amines

EXAMPLES

The following examples illustrate typical syntheses of the compounds of Formula I as described generally above. These examples are illustrative only and are not intended to limit the disclosure in any way. The reagents and starting materials are readily available to one of ordinary skill in the art.

Chemistry

Typical Procedures and Characterization of Selected Examples:

Unless otherwise stated, solvents and reagents were used directly as obtained from commercial sources, and reactions were performed under a nitrogen atmosphere. Flash chromatography was conducted on Silica gel 60 (0.040-0.063 particle size; EM Science supply). $^1$H NMR spectra were recorded on Bruker DRX-500f at 500 MHz (or Bruker AV 400 MHz, Bruker DPX-300B, or Varian Gemini 300 at 300 MHz as stated). The chemical shifts were reported in ppm on the δ scale relative to δTMS=0. The following internal references were used for the residual protons in the following solvents: $CDCl_3$ ($δ_H$ 7.26), $CD_3OD$ ($δ_H$ 3.30), acetic-d4 (Acetic Acid $d_4$) ($δ_H$ 11.6, 2.07), DMSO mix or DMSO-D6-$CDCl_3$ ($δ_H$ 2.50 and 8.25) (ratio 75%:25%), and DMSO-D6 ($δ_H$ 2.50). Standard acronyms were employed to describe the multiplicity patterns: s (singlet), br. s (broad singlet), d (doublet), t (triplet), q (quartet), m (multiplet), b (broad), app (apparent). The coupling constant (J) is in Hertz. All Liquid Chromatography (LC) data were recorded on a Shimadzu LC-10AS liquid chromatograph using a SPD-10AV UV-Vis detector with Mass Spectrometry (MS) data determined using a Micromass Platform for LC in electrospray mode.

LC/MS Methods:

Method 1
Start % B=20, Final % B=100 over 2 minute gradient, hold at 100% B
Flow Rate=1 mL/min
Wavelength=220 nm
Solvent A=95% water, 5% methanol, 10 mM Ammonium Actetate
Solvent B=5% water, 95% methanol, 10 mM Ammonium Actetate
Column=Phenomenex Luna C18, 3 μm, 2.0×30 mm Method 2
Start % B=0, Final % B=100 over 2 minute gradient, hold at 100 % B
Flow Rate=1 mL/min
Wavelength=220 nm
Solvent A=95% water, 5% methanol, 10 mM Ammonium Actetate
Solvent B=5% water, 95% methanol, 10 mM Ammonium Actetate
Column=Phenomenex Luna C18, 3 μm, 2.0×30 mm Method 3
Start % B=30, Final % B=100 over 4 min gradient, hold at 100% B
Flow Rate=0.8 mL/min
Wavelength=220
Solvent Pair=Water-Methanol-0.1% TFA
Solvent A=90% Water-10% Methanol-0.1% TFA
Solvent B=10% Water-90% Methanol-0.1% TFA
Column=PHENOMENEX-LUNA 2.0×50 mm 3 um Method 4
Start % B=0, Final % B=100 over 4 min gradient, hold at 100% B
Flow Rate=0.8 mL/min
Wavelength=220
Solvent Pair=Water-Methanol-0.1% TFA
Solvent A=90% Water-10% Methanol-0.1% TFA
Solvent B=10% Water-90% Methanol-0.1% TFA
Column=PHENOMENEX-LUNA 2.0×50 mm 3 um Method 5
Start % B=0, Final % B=100 over 4 min gradient, hold at 100% B
Flow Rate=0.8 mL/min
Wavelength=220

Solvent Pair=ACN:Water:Ammonium Actetate
Solvent A=5% ACN:95% Water:10 mM Ammonium Actetate
Solvent B=95% ACN:5% Water:10 mM Ammonium Actetate
Column=Phenomenex LUNA C18, 50×2, 3 u
Prep-HPLC Methods:
Method 1
Start % B=20, Final % B=100 over 10 min gradient, hold at 100% B
Flow Rate=50 mL/min
Wavelength=220
Solvent Pair=Water-acetonitrile-TFA
Solvent A=90% Water-10% acetonitrile-0.1% TFA
Solvent B=10% Water-90% acetonitrile-0.1% TFA
Column=Waters Sunfire C18, 5 μm, 30×150 mm
Method 2
Start % B=30, Final % B=100 over 10 min gradient, hold at 100% B
Flow Rate=50 mL/min
Wavelength=220
Solvent Pair=Water-acetonitrile-TFA
Solvent A=90% Water-10% acetonitrile-0.1% TFA
Solvent B=10% Water-90% acetonitrile-0.1% TFA
Column=Waters Sunfire C18, 5 μm, 30×150 mm
Method 3
Start % B=20, Final % B=100 over 15 min gradient, hold at 100% B
Flow Rate=50 mL/min
Wavelength=220
Solvent Pair=Water-acetonitrile-TFA
Solvent A=90% Water-10% acetonitrile-0.1% TFA
Solvent B=10% Water-90% acetonitrile-0.1% TFA
Column=Waters Xbridge Phenyl 5 μm, 30×100 mm
Method 4
Start % B=20, Final % B=100 over 8 min gradient, hold at 100% B
Flow Rate=50 mL/min
Wavelength=220
Solvent Pair=Water-acetonitrile-TFA
Solvent A=90% Water-10% acetonitrile-0.1% TFA
Solvent B=10% Water-90% acetonitrile-0.1% TFA
Column=Waters Xbridge Phenyl 5 μm, 30×100 mm
Method 5
Start % B=15, Final % B=100 over 10 min gradient, hold at 100% B for 4 min
Flow Rate=50 mL/min
Wavelength=220
Solvent Pair=Water-acetonitrile-TFA
Solvent A=90% Water-10% acetonitrile-0.1% TFA
Solvent B=10% Water-90% acetonitrile-0.1% TFA
Column=Waters Xbridge Phenyl 5 μm, 30×100 mm
Method 6
Start % B=10, Final % B=100 over 10 minute gradient, hold at 100% B
Flow Rate=40 mL/min
Wavelength=220 nm
Solvent A=10% MeOH-90% $H_2O$-0.1% TFA
Solvent B=90% MeOH-10% $H_2O$-0.1% TFA
Column=YMC COMBIPREP ODS 30×50 mm S5

Example 1

Preparation of 2-(((1R,3aS,5aR,5bR,7aR,11aS,11bR,13aR,13bR)-9-(4-carboxyphenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-3a-yl) ethynyl)benzoic acid

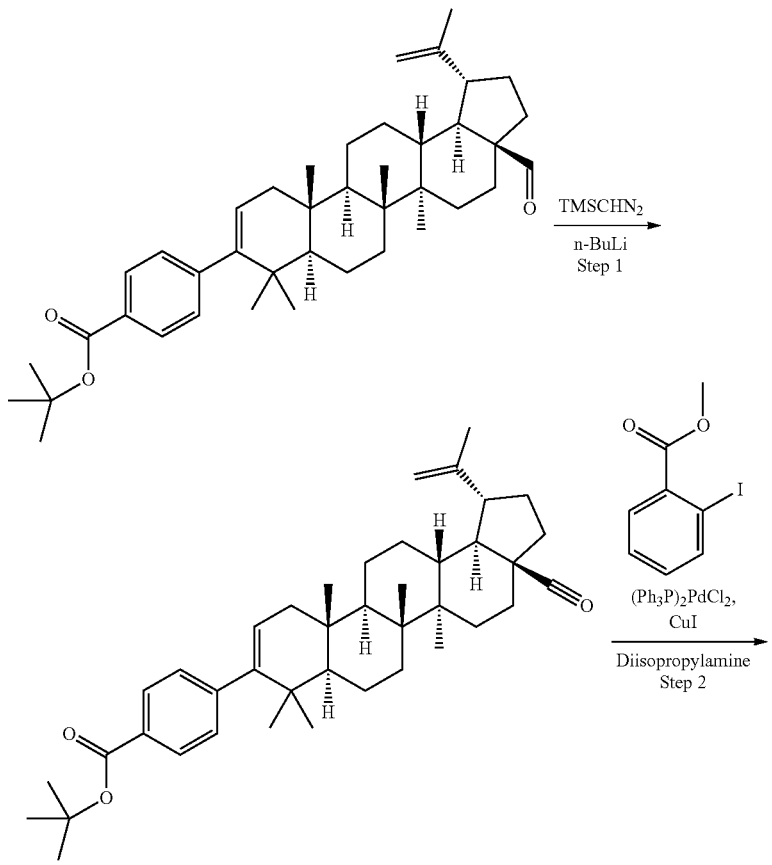

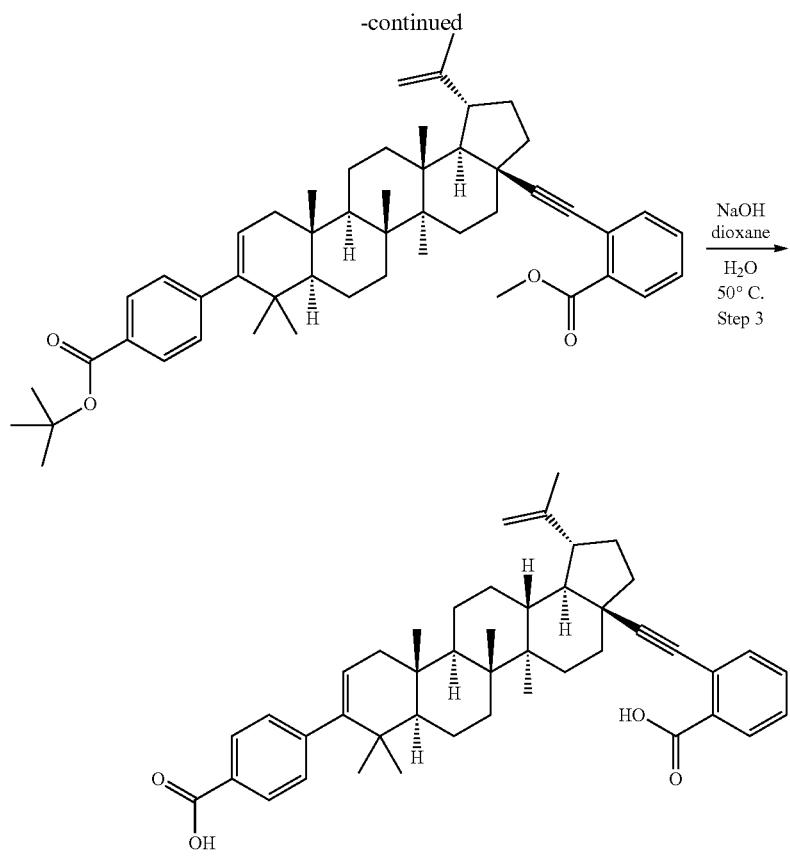

Example 1

Step 1. Preparation of tert-butyl 4-((1R,3aS,5aR,5bR,7aR, 11aS,11bR,13aR,13bR)-3a-ethynyl-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a]chrysen-9-yl)benzoate To a stirred solution of (diazomethyl)trimethylsilane (2 M in THF, 0.250 mL, 0.501 mmol) was added n-butyllithium (0.313 mL, 0.501 mmol) dropwise at −78° C. under argon atmosphere and the solution was stirred at −78° C. for 20 min. A solution of tert-butyl 4-((1R,3aS,5aR,5bR,7aR,11aS,11bR,13aR,13bR)-3a-formyl-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate) (prepared as described in WO 2012106188) (300 mg, 0.501 mmol) in THF (3 mL) was then added to the above solution at −78° C. The mixture was stirred at −78° C. for two hours. The reaction was quenched by addition of water (10 mL). The mixture was extracted with EtOAc (3×20 mL). The combined organic layers were washed with water and brine and dried over $Na_2SO_4$. After removal of solvent, the residue was purified on a silica gel column using 0-5% ethyl acetate/hexanes as the mobile phase. The fractions containing the desired product were combined and concentrated to give the title compound as a white solid. (181 mg, 61%). MS: m/e 617.5 (M+23)$^+$, 5.25 min (method 1). $^1$H NMR (400 MHz, CHLOROFORM-d) δ 7.97-7.77 (m, 2H), 7.22-7.07 (m, 2H), 5.42-5.21 (m, 1H), 4.76 (s, 1H), 4.70-4.48 (m, 1H), 2.66 (d, J=5.5 Hz, 1H), 2.22-1.75 (m, 8H), 1.71 (s, 3H), 1.61 (s, 9H), 1.56-1.15 (m, 15H), 1.14-1.11 (m, 3H), 1.01 (s, 3H), 0.98 (s, 3H), 0.93 (br. s., 6H).

Step 2. Preparation of methyl 2-(((1R,3aS,5aR,5bR,7aR, 11aS,11bR,13aR,13bR)-9-(4-(tert-butoxycarbonyl)phenyl)-5a,5b,8,8,11a-pentamethyl-1-(prop-1-en-2-yl)-2,3,3a,4,5, 5a,5b,6,7,7a,8,11,11a,11b,12,13,13a,13b-octadecahydro-1H-cyclopenta[a]chrysen-3a-yl)ethynyl)benzoate To a stirred solution of tert-butyl 4-((1R,3aS,5aR,5bR, 7aR,11aS,11bR,13aR,13bR)-3a-ethynyl-5a,5b,8,8,11a-pentamethyl-1-(prop-1-en-2-yl)-2,3,3a,4,5,5a,5b,6,7,7a,8,11, 11a,11b,12,13,13a,13b-octadecahydro-1H-cyclopenta[a]chrysen-9-yl)benzoate (250 mg, 0.420 mmol) in anhydrous THF (25 mL) under a nitrogen atmosphere was added methyl 2-iodobenzoate (110 mg, 0.420 mmol), bis(triphenylphosphine)palladium(II) chloride (14.75 mg, 0.021 mmol), copper(I) iodide (8.00 mg, 0.042 mmol) and diisopropylamine (0.089 mL, 0.630 mmol). The yellow solution mixture was heated at 60° C. for 4 hours. The reaction mixture was quenched with 1 N HCl and extracted with ethyl acetate (2×20 mL). The combined organic layers were washed with water and brine then dried over sodium sulfate. The solvent was evaporated to dryness and the residue was purified by a silica gel column to give the title compound as a white solid (70 mg, 21%). MS: m/e 729.8 (M+H)$^+$, 5.501 min (method 1). ¹H NMR (400 MHz, CHLOROFORM-d) δ 7.97-7.81 (m, 3H), 7.57 (dd, J=7.8, 1.0 Hz, 1H), 7.46 (td, J=7.5, 1.3 Hz, 1H), 7.35 (td, J=7.7, 1.3 Hz, 1H), 7.25-7.10 (m, 2H), 5.29 (d, J=4.8 Hz, 1H), 4.91-4.73 (m, 1H), 4.69-4.56 (m, 1H), 3.96 (s, 3H), 3.07-2.61 (m, 1H), 2.46-1.93 (m, 5H), 1.89-1.66 (m, 3H), 1.74 (s, 3H), 1.61 (s, 9H), 1.57-1.21 (m, 14H), 1.14 (s, 3H), 1.02 (s, 3H), 1.00-0.97 (m, 3H), 0.94 (d, J=3.0 Hz, 6H).

Step 3: To a solution of methyl 2-(((1R,3aS,5aR,5bR,7aR,11aS,11bR,13aR,13bR)-9-(4-(tert-butoxycarbonyl)phenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-3a-yl)ethynyl)benzoate (70 mg, 0.096 mmol) in dioxane (2 mL) and MeOH (1 mL) was added 1N NaOH (1 mL, 1 mmol). The mixture was stirred at 85° C. for 15 h. The resulted solution was purified by prep HPLC (method 1) to give 2-(((1R,3aS,5aR,5bR,7aR,11aS,11bR,13aR,13bR)-9-(4-carboxyphenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-3a-yl)ethynyl)benzoic acid as a white solid (6.0 mg, 9.5%). MS: m/e 659.7 (M+H)⁺, 2.50 min (method 2). ¹H NMR (400 MHz, METHANOL-d₄) δ 7.92 (d, J=8.3 Hz, 2H), 7.77 (dd, J=7.8, 1.0 Hz, 1H), 7.54-7.49 (m, 1H), 7.44 (td, J=7.5, 1.5 Hz, 1H), 7.39-7.31 (m, 1H), 7.22 (d, J=8.3 Hz, 2H), 5.31 (dd, J=6.1, 1.6 Hz, 1H), 4.79 (d, J=2.3 Hz, 1H), 4.63 (dd, J=2.1, 1.4 Hz, 1H), 2.83 (td, J=11.0, 5.4 Hz, 1H), 2.41-2.11 (m, 4H), 2.04-1.92 (m, 2H), 1.84 (d, J=11.3 Hz, 1H), 1.78-1.69 (m, 1H), 1.74 (s, 3H), 1.65-1.21 (m, 14H), 1.18 (s, 3H), 1.06 (s, 3H), 1.04 (s, 3H), 0.98 (s, 3H), 0.96 (s, 3H).

Example 2

Preparation of 4-((1R,3aS,5aR,5bR,7aR,11aS,11bR,13aR,13bR)-3a-((2-(1H-tetrazol-5-yl)thiophen-3-yl)ethynyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

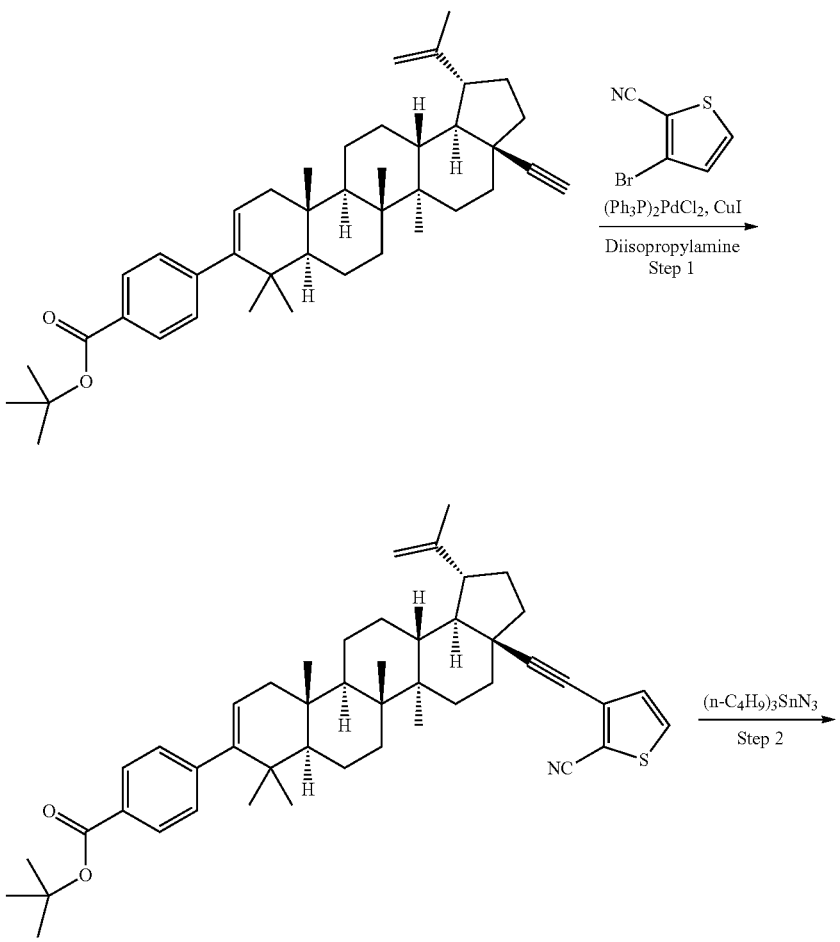

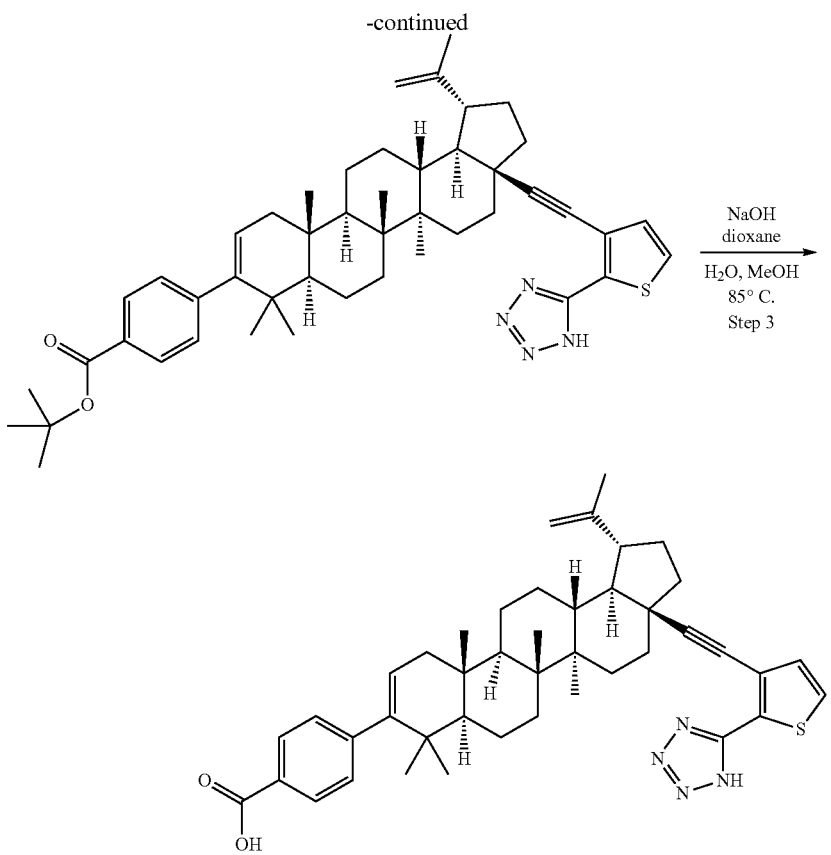

Example 2

Step 1. Preparation of tert-butyl 4-((1R,3aS,5aR,5bR,7aR,11aS,11bR,13aR,13bR)-3a-((2-cyanothiophen-3-yl)ethynyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate The title compound was prepared in 71% yield following the procedure described above in step 2 of the preparation of 4-((1R,3aR,5aR,5bR,7aR,11aS,11bR,13aR,13bR)-3a-(2-(1,1-dioxidothiomorpholino)ethyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid, using 3-bromothiophene-2-carbonitrile as the reactant. MS: m/e 646.6 (M+H-56)$^+$, 4.68 min (method 2). $^1$H NMR (400 MHz, CHLOROFORM-d) δ 7.88 (d, J=8.3 Hz, 2H), 7.64-7.46 (m, 1H), 7.16 (d, J=8.0 Hz, 2H), 7.13-6.99 (m, 1H), 5.27 (d, J=4.8 Hz, 1H), 4.83-4.72 (m, 1H), 4.68-4.55 (m, 1H), 2.96-2.65 (m, 1H), 2.33-2.20 (m, 1H), 2.14-1.73 (m, 6H), 1.72-1.63 (m, 1H), 1.71 (s, 3H), 1.62-1.57 (m, 9H), 1.55-1.34 (m, 8H), 1.33-1.18 (m, 5H), 1.15-1.04 (m, 1H), 1.00 (d, J=3.3 Hz, 3H), 0.99-0.95 (m, 6H), 0.91 (s, 6H).

Step 2. Preparation of tert-butyl 4-((1R,3aS,5aR,5bR,7aR,11aS,11bR,13aR,13bR)-3a-((2-(1H-tetrazol-5-yl)thiophen-3-yl)ethynyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate To a resealable pressure tube was added tert-butyl 4-((1R,3aS,5aR,5bR,7aR,11aS,11bR,13aR,13bR)-3a-((2-cyanothiophen-3-yl)ethynyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (251 mg, 0.358 mmol) and azidotributylstannane (313 mg, 0.941 mmol) in toluene (1 mL) under nitrogen. The pressure tube was sealed and warmed to 130° C. overnight. The crude reaction mixture was evaporated to dryness, washed with water (10 mL) extracted with EtOAc (2×10 mL). The organic layers were combined and dried over sodium sulfate. The solvent was evaporated to dryness and the residue was purified in a silica gel column to give titled compound as a white solid (170 mg, 63.8%). MS: m/e 745.87 (M+H)$^+$, 3.05 min (method 2). $^1$H NMR (400 MHz, CHLOROFORM-d) δ 7.90 (d, J=8.3 Hz, 2H), 7.56 (d, J=5.0 Hz, 1H), 7.23 (d, J=5.0 Hz, 1H), 7.20-7.13 (m, 2H), 5.29 (dd, J=6.1, 1.6 Hz, 1H), 4.78 (d, J=1.5 Hz, 1H), 4.67 (s, 1H), 2.68 (td, J=11.0, 5.6 Hz, 1H), 2.29-1.95 (m, 3H), 1.86-1.69 (m, 2H), 1.74 (s, 3H), 1.69-1.58 (m, 4H), 1.61 (s, 9H), 1.57-1.14 (m, 14H), 1.11 (s, 3H), 1.04 (s, 3H), 0.99 (s, 3H), 0.95-0.93 (m, 6H).

Step 3: 4-((1R,3aS,5aR,5bR,7aR,11aS,11bR,13aR,13bR)-3a-((2-(1H-tetrazol-5-yl)thiophen-3-yl)ethynyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid (solid, 25.4% yield) was obtained following the method described above in step 3 of the preparation of 2-(((1R,3aS,5aR,5bR,7aR,11aS,11bR,13 aR,13bR)-9-(4-carboxyphenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-3a-yl)ethynyl)benzoic acid, using tert-butyl 4-((1R,3aS,5aR,5bR,7aR,11aS,11bR,13 aR,13bR)-3a-((2-(1H-tetrazol-5-yl)thiophen-3-yl)ethynyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]

chrysen-9-yl)benzoate as the reactant. MS: m/e 689.45 (M+H-56)⁺, 3.046 min (method 2). ¹H NMR (400 MHz, CHLOROFORM-d) δ 9.67 (s., 1H), 8.02 (d, J=8.3 Hz, 2H), 7.62 (d, J=5.0 Hz, 1H), 7.38-7.16 (m, 3H), 5.33 (d, J=4.5 Hz, 1H), 4.79 (s, 1H), 4.69 (s, 1H), 2.67 (td, J=10.9, 5.8 Hz, 1H), 2.35-1.79 (m, 8H), 1.75 (s, 3H), 1.72-1.14 (m, 15H), 1.12 (s, 3H), 1.06 (s, 3H), 1.00 (s, 3H), 0.96 (s, 6H).
Example 3
Preparation of 4-(((1R,3aS,5aR,5bR,7aR,11aS,11bR,13aR,13bR)-5a,5b,8,8,11a-pentamethyl-3a-(1,3,4-oxadiazol-2-yl)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid
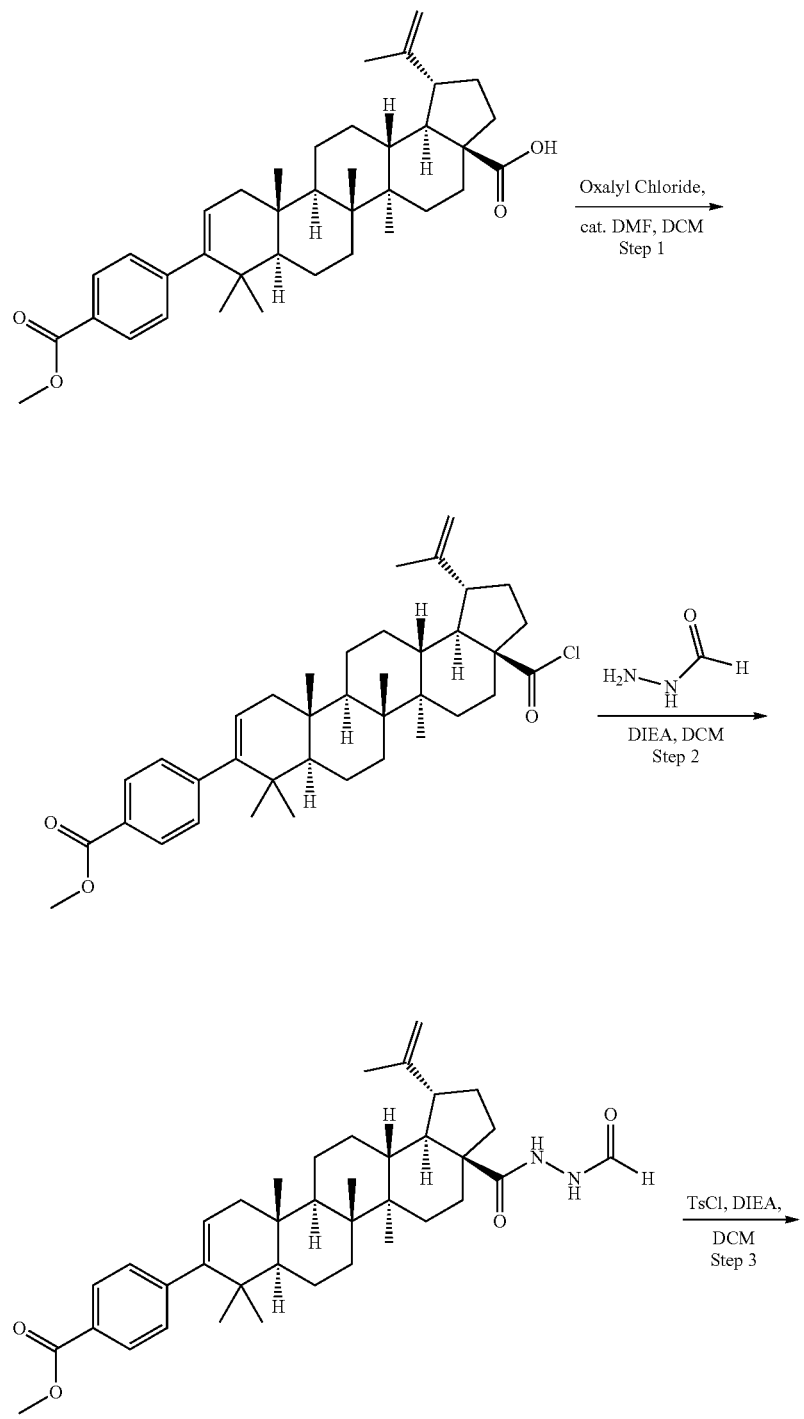

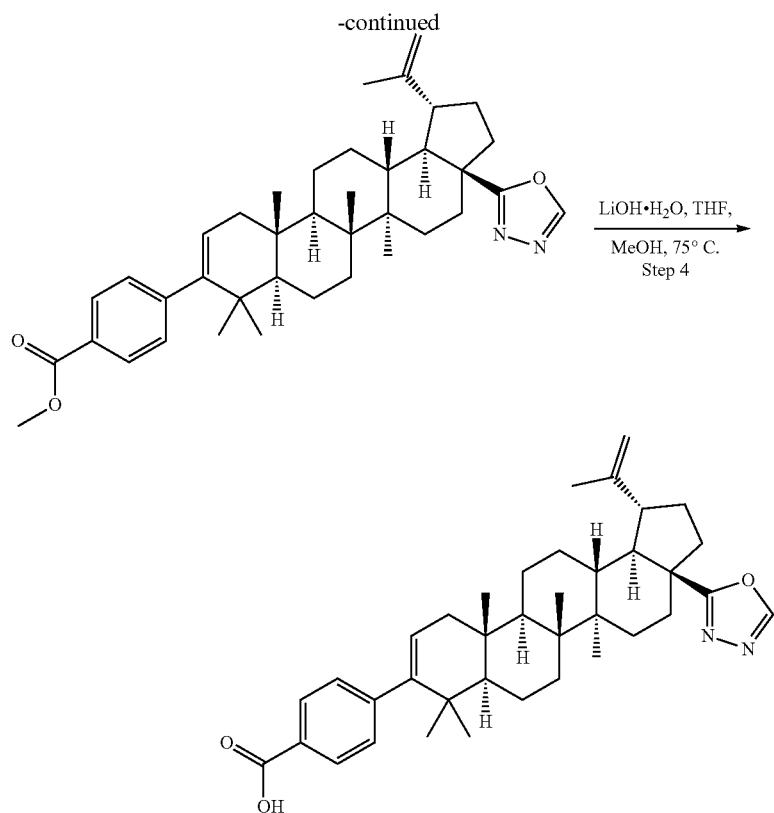

Example 3

Step 1. Preparation of methyl 4-((1R,3aS,5aR,5bR,7aR, 11aS,11bR,13aR,13bR)-3a-(chlorocarbonyl)-5a,5b,8,8,11a-pentamethyl-1-(prop-1-en-2-yl)-2,3,3a,4,5,5a,5b,6,7,7a,8, 11,11a,11b,12,13,13a,13b-octadecahydro-1H-cyclopenta[a]chrysen-9-yl)benzoate.

To a slurry of (1R,3aS,5aR,5bR,7aR,11aS,11bR,13aR, 13bR)-9-(4-(methoxycarbonyl)phenyl)-5a,5b,8,8,11a-pentamethyl-1-(prop-1-en-2-yl)-2,3,3a,4,5,5a,5b,6,7,7a,8,11, 11a,11b,12,13,13a,13b-octadecahydro-1H-cyclopenta[a]chrysene-3a-carboxylic acid (400 mg, 0.698 mmol) at 0° C. in DCM (15 mL was added oxalyl chloride (0.177 mL, 2.095 mmol) and N,N-dimethylformamide (0.054 mL, 0.698 mmol). The cold bath was removed and reaction was stirred at rt. Gas evolved vigorously and reaction became a clear and homogeneous solution. After 4 h, a small aliquot was taken and quenched with MeOH and TLC (9:1 hex:EtOAc) showed reaction was complete. The reaction was concentrated and dried in vacuo to give the title compound (410 mg, 99% yield) as an off-white solid. The material was used in the next step without further purification.

Step 2. Preparation of methyl 4-((1R,3aS,5aR,5bR,7aR, 11aS,11bR,13aR,13bR)-3a-(2-formylhydrazinecarbonyl)-5a,5b,8,8,11a-pentamethyl-1-(prop-1-en-2-yl)-2,3,3a,4,5, 5a,5b,6,7,7a,8,11,11a,11b,12,13,13a,13b-octadecahydro-1H-cyclopenta[a]chrysen-9-yl)benzoate.

To a solution of methyl 4-((1R,3aS,5aR,5bR,7aR,11aS, 11bR,13aR,13bR)-3a-(chlorocarbonyl)-5a,5b,8,8,11a-pentamethyl-1-(prop-1-en-2-yl)-2,3,3a,4,5,5a,5b,6,7,7a,8,11, 11a,11b,12,13,13a,13b-octadecahydro-1H-cyclopenta[a]chrysen-9-yl)benzoate (110 mg, 0.186 mmol) in DCM (2 mL) was added N,N-diisopropylethylamine (0.130 mL, 0.744 mmol) and formic acid hydrazide (33.5 mg, 0.558 mmol) and the mixture was stirred at rt overnight. After 16 h, the reaction was concentrated. The crude material was purified by reverse phase prep-HPLC using HPLC method 1 to give the title compound (86.4 mg, 76% yield) as a white solid. LC/MS: m/e 614.0 (M+H)$^+$, 5.58 min (method 3). $^1$H NMR (400 MHz, CHLOROFORM-d) δ 9.20 (br. s., 1H), 7.93 (d, J=8.3 Hz, 2H), 7.20 (d, J=8.3 Hz, 2H), 5.29 (d, J=4.6 Hz, 1H), 4.78 (s, 1H), 4.66 (s, 1H), 3.91 (s, 3H), 3.24 (s, 4H), 2.95 (td, J=11.0, 5.4 Hz, 1H), 2.37 (td, J=12.2, 3.2 Hz, 1H), 2.24-2.05 (m, 2H), 2.02-1.93 (m, 1H), 1.92-1.75 (m, 3H), 1.73 (s, 3H), 1.71-1.62 (m, 2H), 1.58-1.33 (m, 9H), 1.30-1.18 (m, 2H), 1.09 (s, 1H), 1.03 (s, 2H), 0.98 (s, 3H), 0.95 (s, 3H), 0.93 (s, 5H).

Step 3. Preparation of methyl 4-((1R,3aS,5aR,5bR,7aR, 11aS,11bR,13aR,13bR)-5a,5b,8,8,11a-pentamethyl-3a-(1,3, 4-oxadiazol-2-yl)-1-(prop-1-en-2-yl)-2,3,3a,4,5,5a,5b,6,7, 7a,8,11,11a,11b,12,13,13a,13b-octadecahydro-1H-cyclopenta[a]chrysen-9-yl)benzoate.

To a slurry of methyl 4-((1R,3aS,5aR,5bR,7aR,11aS, 11bR,13aR,13bR)-3a-(2-formylhydrazinecarbonyl)-5a,5b, 8,8,11a-pentamethyl-1-(prop-1-en-2-yl)-2,3,3a,4,5,5a,5b,6, 7,7a,8,11,11a,11b,12,13,13a,13b-octadecahydro-1H-cyclopenta[a]chrysen-9-yl)benzoate (83 mg, 0.135 mmol) and N,N-diisopropylethylamine (0.188 mL, 1.080 mmol) in acetonitrile (2 mL) was added p-toluenesulfonyl chloride (129 mg, 0.675 mmol). The mixture was treated with DCM (1 mL) and the reaction became a homogeneous solution which was stirred at rt for 16 h. The reaction was concentrated and purified by reverse phase prep-HPLC using HPLC method 2 and dried in vacuo to give the title compound (51.3 mg, 58.6% yield) as a white solid. LC/MS: m/e 597.3 (M+H)$^+$, 6.70 min (method 3). $^1$H NMR (400 MHz, CHLO- ROFORM-d) δ 8.38 (s, 1H), 7.93 (d, J=8.3 Hz, 2H), 7.20 (d, J=8.3 Hz, 2H), 5.29 (dd, J=6.4, 1.7 Hz, 1H), 4.81 (d, J=1.7 Hz, 1H), 4.69-4.63 (m, 1H), 3.91 (s, 3H), 3.15 (td, J=11.1, 5.1 Hz, 1H), 2.46-2.32 (m, 2H), 2.11 (dd, J=17.1, 6.4 Hz, 1H), 2.01-1.91 (m, 2H), 1.90-1.78 (m, 2H), 1.75 (s, 3H), 1.73-1.62 (m, 3H), 1.50-1.31 (m, 9H), 1.25-1.18 (m, 2H), 1.16-1.09 (m, 1H), 1.06 (s, 3H), 0.96 (s, 3H), 0.92 (s, 6H), 0.86 (s, 3H).

Step 4: To a solution of methyl 4-((1R,3aS,5aR,5bR,7aR,11aS,11bR,13aR,13bR)-5a,5b,8,8,11a-pentamethyl-3a-(1,3,4-oxadiazol-2-yl)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (48 mg, 0.080 mmol) in THF (1 mL) and MeOH (0.5 mL) was added a solution of 1N lithium hydroxide (0.241 mL, 0.241 mmol). The reaction mixture was stirred at 75° C. After 1 h, the reaction was cooled to rt and purified by reverse phase prep-HPLC using HPLC method 2 to give 4-((1R,3aS,5aR,5bR,7aR,11aS,11bR,13aR,13bR)-5a,5b,8,8,11a-pentamethyl-3a-(1,3,4-oxadiazol-2-yl)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid (21.8 mg, 43.3% yield) as a white solid. LC/MS: m/e 583.3 (M+H)+, 5.38 min (method 3). $^1$H NMR (400 MHz, CHLOROFORM-d) δ 8.39 (s, 1H), 8.00 (d, J=8.3 Hz, 2H), 7.23 (d, J=8.3 Hz, 2H), 5.31 (d, J=4.6 Hz, 1H), 4.81 (d, J=1.5 Hz, 1H), 4.66 (s, 1H), 3.16 (td, J=11.1, 5.1 Hz, 1H), 2.46-2.32 (m, 3H), 2.12 (dd, J=17.1, 6.4 Hz, 1H), 1.97-1.89 (m, 2H), 1.84-1.79 (m, 1H), 1.73-1.68 (m, 2H), 1.68-1.60 (m, 2H), 1.55-1.46 (m, 3H), 1.44 (s, 3H), 1.40-1.31 (m, 4H), 1.25-1.19 (m, 2H), 1.14 (d, J=6.1 Hz, 1H), 1.06 (s, 3H), 1.00 (d, J=11.0 Hz, 1H), 0.96 (s, 3H), 0.93 (s, 6H), 0.86 (s, 3H). $^{13}$C NMR (101 MHz, CHLOROFORM-d) δ 170.5, 170.1, 152.3, 149.8, 149.6, 146.2, 130.2, 129.1, 126.8, 125.5, 124.2, 110.2, 77.2, 52.9, 50.5, 49.8, 49.5, 46.8, 42.6, 41.7, 40.6, 38.2, 37.9, 37.5, 36.3, 33.6, 32.7, 30.3, 30.2, 29.4, 28.9, 25.4, 21.2, 21.0, 19.7, 19.5, 16.4, 15.6, 14.8.

Example 4

Preparation of 4-((1R,3aS,5aR,5bR,7aR,11aS,11bR,13aR,13bR)-3a-(5-((dimethylamino)methyl)-1,3,4-oxadiazol-2-yl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

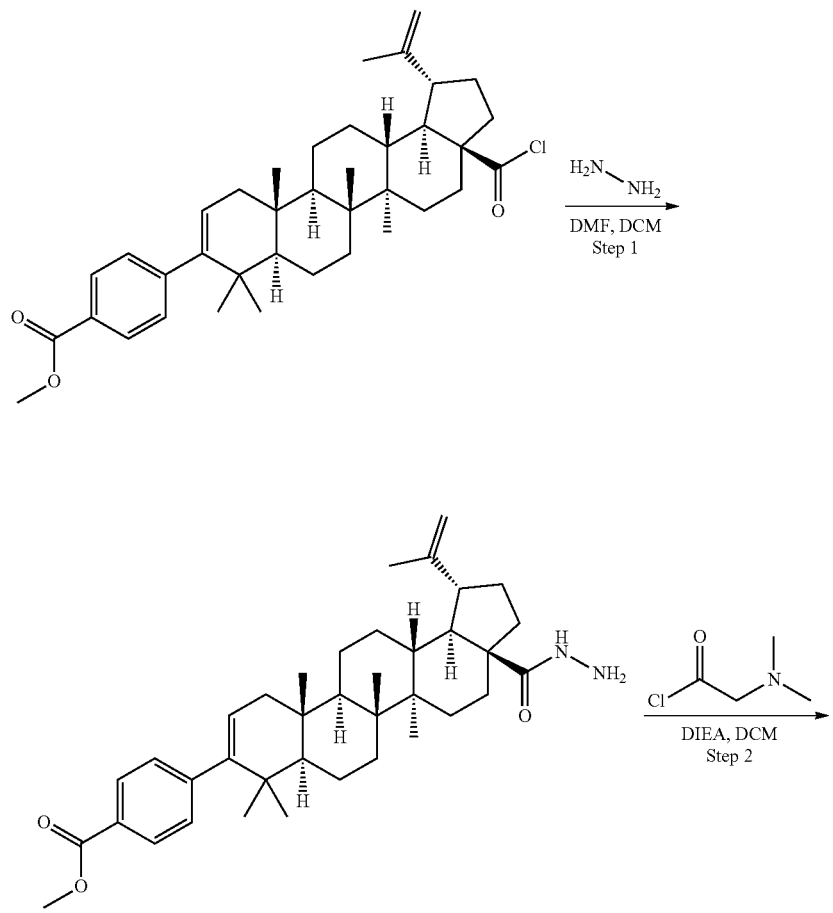

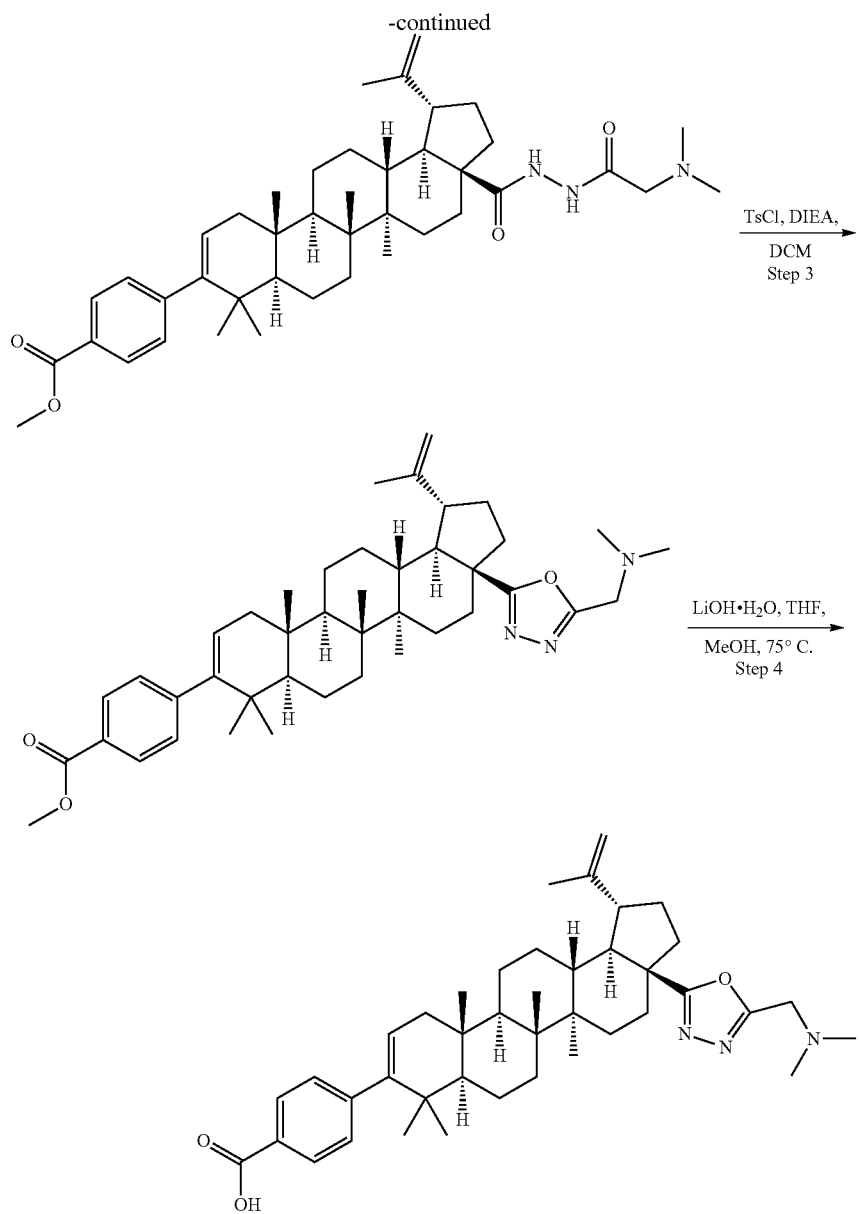

Example 4

Step 1. Preparation of methyl 4-((1R,3aS,5aR,5bR,7aR, 11aS,11bR,13aR,13bR)-3a-(hydrazinecarbonyl)-5a,5b,8,8, 11a-pentamethyl-1-(prop-1-en-2-yl)-2,3,3a,4,5,5a,5b,6,7, 7a,8,11,11a,11b,12,13,13a,13b-octadecahydro-1H-cyclopenta[a]chrysen-9-yl)benzoate.

To a solution of methyl 4-((1R,3aS,5aR,5bR,7aR,11aS, 11bR,13aR,13bR)-3a-(chlorocarbonyl)-5a,5b,8,8,11a-pentamethyl-1-(prop-1-en-2-yl)-2,3,3a,4,5,5a,5b,6,7,7a,8,11, 11a,11b,12,13,13a,13b-octadecahydro-1H-cyclopenta[a]chrysen-9-yl)benzoate (400 mg, 0.677 mmol) and N,N-diisopropylethylamine (0.354 mL, 2.030 mmol) was added quickly hydrazine monohydrate (0.670 mL, 13.53 mmol). The resulting cloudy reaction mixture was stirred at rt. After 1 h, the reaction was concentrated, the resulting white solid was dissolved in DCM (50 mL) and washed with 1N HCl (15 mL). The resulting emulsion mixture was treated with brine, shaken, and the layers were separated. The aqueous layer was extracted with DCM (50 mL). The combined organic layers were washed with brine, dried over MgSO$_4$, filtered, concentrated and dried in vacuo to give the title compound (358 mg, 90% yield) as a white solid. LC/MS: m/e 587.3 (M+H)$^+$, 4.65 min (method 3).

$^1$H NMR (400 MHz, CHLOROFORM-d) δ 7.96-7.90 (m, 2H), 7.20 (d, J=8.3 Hz, 2H), 6.88 (s, 1H), 5.32-5.27 (m, 1H), 4.77 (d, J=2.0 Hz, 1H), 4.62 (t, J=1.7 Hz, 1H), 3.91 (s, 3H), 3.12 (td, J=10.8, 4.0 Hz, 1H), 2.53-2.37 (m, 1H), 2.12 (dd, J=17.1, 6.4 Hz, 1H), 1.95 (d, J=13.2 Hz, 2H), 1.80-1.73 (m, 2H), 1.71 (s, 3H), 1.69-1.61 (m, 2H), 1.59-1.52 (m, 2H), 1.51-1.36 (m, 9H), 1.33 (dd, J=12.1, 4.3 Hz, 1H), 1.22 (d, J=12.5 Hz, 2H), 1.01 (s, 3H), 1.00 (s, 3H), 0.98 (s, 3H), 0.93 (s, 3H), 0.93 (s, 3H). $^{13}$C NMR (101 MHz, CHLOROFORM-d) δ 177.2, 167.2, 150.6, 148.7, 146.2, 130.1, 128.5, 127.9, 124.1, 109.6, 77.2, 55.0, 52.9, 52.0, 50.3, 49.6, 46.8, 42.4, 41.7, 40.6, 38.3, 38.1, 37.5, 36.3, 33.7, 33.3, 30.8, 29.4, 25.7, 21.3, 21.0, 19.8, 19.5, 16.4, 15.9, 14.7.

Step 2. Preparation of methyl 4-((1R,3aS,5aR,5bR,7aR,11aS,11bR,13aR,13bR)-3a-(2-(2-(dimethylamino)acetyl)hydrazinecarbonyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate.

To a solution of methyl 4-((1R,3aS,5aR,5bR,7aR,11aS,11bR,13aR,13bR)-3a-(hydrazinecarbonyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (102 mg, 0.174 mmol) in DCM (2 mL) was added N,N-diisopropylethylamine (0.121 mL, 0.695 mmol) and dimethylaminoacetyl chloride hydrochloride (30.2 mg, 0.191 mmol). The resulting brown reaction mixture was stirred at rt. After 2h, the reaction mixture was concentrated and dried under vacuo to give the title compound as an off-white foam. The material was used in the next step without further purification. LC/MS: m/e 672.4 (M+H)$^+$, 4.63 min (method 3).

Step 3. Preparation of methyl 4-((1R,3aS,5aR,5bR,7aR,11aS,11bR,13aR,13bR)-3a-(5-((dimethylamino)methyl)-1,3,4-oxadiazol-2-yl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate.

To a solution of methyl 4-((1R,3aS,5aR,5bR,7aR,11aS,11bR,13aR,13bR)-3a-(2-(2-(dimethylamino)acetyl)hydrazinecarbonyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (33 mg, 0.049 mmol) and N,N-diisopropylethylamine (0.068 mL, 0.393 mmol) in acetonitrile (1 mL) was added p-toluenesulfonyl chloride (46.8 mg, 0.246 mmol). The reaction became a homogeneous solution and was stirred at rt. After 17 h, the reaction mixture was diluted with THF (0.5 mL) and purified by reverse phase prep-HPLC using HPLC method 3 and dried in vacuo to give methyl 4-((1R,3aS,5aR,5bR,7aR,11aS,11bR,13aR,13bR)-3a-(5-((dimethylamino)methyl)-1,3,4-oxadiazol-2-yl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate, TFA (17.7 mg, 0.022 mmol, 45.5% yield) as an off white solid. LC/MS: m/e 654.4 (M+H)$^+$, 4.76 min (method 4). $^1$H NMR (400 MHz, CHLOROFORM-d) δ 7.92 (d, J=8.3 Hz, 2H), 7.19 (d, J=8.3 Hz, 2H), 5.29 (d, J=4.6 Hz, 1H), 4.80 (s, 1H), 4.67 (s, 1H), 4.50 (br. s., 2H), 3.91 (s, 3H), 3.13 (td, J=11.0, 5.1 Hz, 1H), 2.91 (s, 6H), 2.39 (td, J=12.1, 3.4 Hz, 1H), 2.31 (d, J=11.2 Hz, 1H), 2.11 (dd, J=17.1, 6.4 Hz, 1H), 1.99-1.88 (m, 2H), 1.81 (d, J=10.0 Hz, 2H), 1.74 (s, 3H), 1.71-1.63 (m, 2H), 1.56-1.35 (m, 8H), 1.31 (dd, J=12.2, 3.9 Hz, 1H), 1.27-1.18 (m, 3H), 1.12 (dd, J=12.5, 3.7 Hz, 1H), 1.05 (s, 3H), 0.95 (s, 3H), 0.92 (s, 3H), 0.91 (s, 3H), 0.84 (s, 3H). $^{13}$C NMR (101 MHz, CHLOROFORM-d) δ 172.5, 167.2, 149.4, 148.7, 146.2, 130.0, 128.5, 127.9, 124.0, 110.3, 77.22-77.17, 52.8, 52.0, 50.9, 49.7, 49.4, 46.7, 42.5, 42.4, 41.7, 40.6, 38.2, 37.7, 37.5, 36.2, 33.5, 32.4, 30.0, 29.4, 28.9, 25.4, 21.2, 21.0, 19.7, 19.4, 16.4, 15.6, 14.8.

Step 4: To a solution of methyl 4-((1R,3aS,5aR,5bR,7aR,11aS,11bR,13aR,13bR)-3a-(5-((dimethylamino)methyl)-1,3,4-oxadiazol-2-yl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate, TFA (54.7 mg, 0.071 mmol) in THF (1 mL) and MeOH (0.25 mL) was added a solution of 3N lithium hydroxide (0.083 mL, 0.249 mmol). The reaction was stirred at 75° C. After 1 h, the reaction was cooled to rt and purified by reverse phase prep-HPLC using HPLC method 4 and dried under vacuo to give 4-((1R,3aS,5aR,5bR,7aR,11aS,11bR,13aR,13bR)-3a-(5-((dimethylamino)methyl)-1,3,4-oxadiazol-2-yl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid, TFA (45.5 mg, 0.057 mmol, 80% yield) as a white solid. LC/MS: m/e 640.4 (M+H)$^+$, 4.33 min (method 3). $^1$H NMR (400 MHz, 1:1 CDCl$_3$:METHANOL-d$_4$) δ 7.89 (d, J=8.3 Hz, 2H), 7.17 (d, J=8.3 Hz, 2H), 5.27 (dd, J=6.2, 1.6 Hz, 1H), 4.77 (d, J=1.5 Hz, 1H), 4.53 (s, 2H), 3.09 (td, J=11.0, 5.1 Hz, 1H), 2.90 (s, 6H), 2.39 (td, J=12.1, 3.4 Hz, 1H), 2.30 (d, J=13.4 Hz, 1H), 2.10 (dd, J=17.1, 6.4 Hz, 1H), 2.00-1.89 (m, 2H), 1.84-1.75 (m, 2H), 1.73 (s, 3H), 1.71-1.64 (m, 2H), 1.56-1.35 (m, 8H), 1.33-1.18 (m, 4H), 1.16-1.09 (m, 1H), 1.06 (s, 3H), 0.95 (s, 3H), 0.90 (s, 6H), 0.85 (s, 3H).

Example 5

Preparation of 4-((1R,3aS,5aR,5bR,7aR,11aS,11bR,13aR,13bR)-5a,5b,8,8,11a-pentamethyl-1-(prop-1-en-2-yl)-3a-(1H-1,2,4-triazol-3-yl)-2,3,3a,4,5,5a,5b,6,7,7a,8,11,11a,11b,12,13,13a,13b-octadecahydro-1H-cyclopenta[a]chrysen-9-yl)benzoic acid

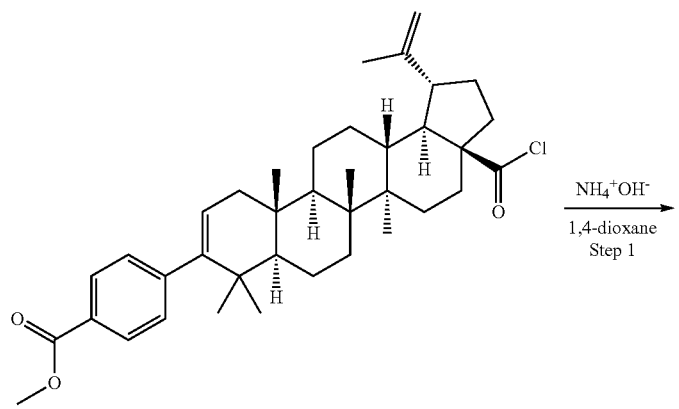

-continued
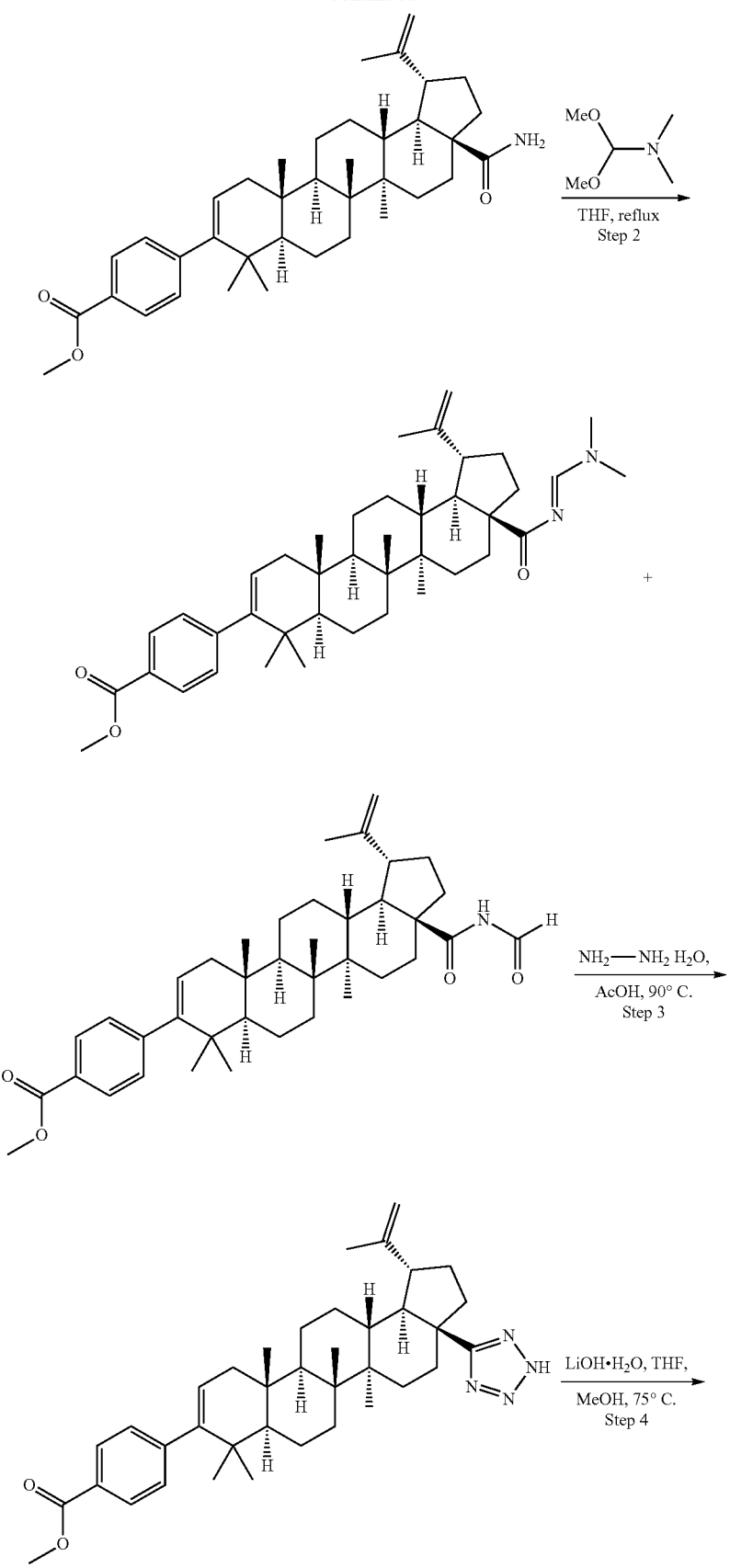

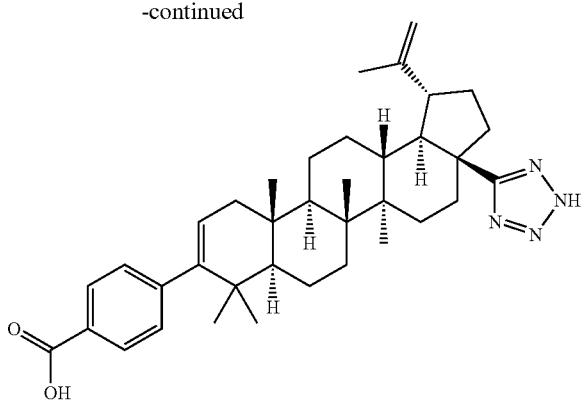

Example 5

Step 1. Preparation of methyl 4-((1R,3aS,5aR,5bR,7aR, 11aS,11bR,13aR,13bR)-3a-carbamoyl-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate.

To a cloudy solution of methyl 4-((1R,3aS,5aR,5bR,7aR, 11aS,11bR,13aR,13bR)-3a-(chlorocarbonyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (300 mg, 0.507 mmol) in 1,4-dioxane (20 mL) was added ammonium hydroxide (2.305 mL, 17.76 mmol) and the mixture was stirred at rt overnight. The reaction was concentrated to dryness. The white residue formed was triturated with H$_2$O (15 mL), filtered, washed with H$_2$O (2×15 mL) and dried in a vacuum oven at 50° C. to give the title compound (290 mg, 100% yield) as a white solid. LC/MS: m/e 572.3 (M+H)$^+$, 6.09 min (method 3). $^1$H NMR (400 MHz, CHLOROFORM-d) δ 7.93 (d, J=8.1 Hz, 2H), 7.20 (d, J=8.1 Hz, 2H), 5.51 (br. s., 1H), 5.30 (d, J=4.9 Hz, 1H), 5.18 (br. s., 1H), 4.77 (br. s., 1H), 4.62 (br. s., 1H), 3.91 (s, 3H), 3.12 (td, J=11.0, 4.2 Hz, 1H), 2.61-2.46 (m, 1H), 2.12 (dd, J=17.2, 6.2 Hz, 1H), 2.07-1.99 (m, 1H), 1.95 (d, J=12.7 Hz, 1H), 1.83 (dd, J=11.9, 7.9 Hz, 1H), 1.76 (br. s., 1H), 1.71 (s, 3H), 1.67-1.61 (m, 3H), 1.52 (d, J=10.5 Hz, 3H), 1.44 (d, J=7.8 Hz, 4H), 1.39 (br. s., 2H), 1.24 (d, J=10.8 Hz, 2H), 1.04 (s, 3H), 1.02 (s, 3H), 0.99 (s, 3H), 0.93 (s, 6H).

Step 2. Preparation of methyl 4-((1R,3aS,5aR,5bR,7aR, 11aS,11bR,13aR,13bR)-3a-((E)-((dimethylamino)methylene)carbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate and methyl 4-((1R,3aS,5aR,5bR,7aR,11aS,11bR,13aR,13bR)-3a-(formylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate.

To a slurry of methyl 4-((1R,3aS,5aR,5bR,7aR,11aS, 11bR,13aR,13bR)-3a-carbamoyl-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (0.285 g, 0.498 mmol) in THF (5 mL) in a medium pressure tube was added N,N-dimethylformamidedimethylacetal (1.057 mL, 7.48 mmol). The resulting slurry was stirred at 85° C. The reaction mixture turned clear and became homogeneous after 5 mins at 85° C. After 18 h, the reaction was concentrated to a white foam material which was purified by flash column chromatography, using 4:1 hex:EtOAc as the mobile phase to give two products. Product one, top spot by TLC (R$_f$=0.82 in 2:1 hex:EtOAc) was identified as: methyl 4-((1R,3aS,5aR,5bR,7aR,11aS,11bR,13aR,13bR)-3a-(formylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (119.2 mg, 39.9% yield, white solid). LC/MS: m/e 598.5 (M-H)$^-$, 5.07 min (method 5). $^1$H NMR (400 MHz, CHLOROFORM-d) δ 9.22 (d, J=9.8 Hz, 1H), 8.36 (d, J=9.8 Hz, 1H), 7.98-7.92 (m, 2H), 7.22 (d, J=8.6 Hz, 2H), 5.31 (d, J=2.0 Hz, 1H), 4.79 (d, J=1.7 Hz, 1H), 4.66 (d, J=1.5 Hz, 1H), 3.93 (s, 3H), 3.06 (td, J=11.0, 4.4 Hz, 1H), 2.59-2.47 (m, 1H), 2.14 (dd, J=17.1, 6.4 Hz, 1H), 2.03-1.91 (m, 2H), 1.85 (dd, J=12.1, 7.7 Hz, 1H), 1.81-1.75 (m, 1H), 1.72 (s, 4H), 1.59 (s, 4H), 1.55-1.37 (m, 9H), 1.35-1.29 (m, 2H), 1.27-1.19 (m, 1H), 1.04 (s, 3H), 1.02 (s, 3H), 1.01 (s, 3H), 0.95 (s, 3H), 0.94 (s, 3H). $^{13}$C NMR (101 MHz, CHLOROFORM-d) δ 176.1, 167.2, 163.1, 149.9, 148.7, 146.3, 130.0, 128.5, 127.9, 124.0, 110.0, 77.2, 56.8, 53.4, 52.9, 52.0, 49.6, 46.2, 42.5, 41.8, 40.6, 37.6, 37.5, 36.8, 36.3, 33.6, 32.2, 30.3, 29.5, 29.4, 25.7, 21.3, 21.0, 19.8, 19.4, 16.5, 15.8, 14.6. Second product, bottom spot by TLC (R$_f$=0.55 in 2:1 hex:EtOAc) was identified as: methyl 4-((1R,3aS,5aR, 5bR,7aR,11aS,11bR,13aR,13bR)-3a-((E)-((dimethylamino)methylene)carbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (150.2 mg, 48.1% yield, white foam). LC/MS: m/e 627.4 (M+H)$^+$, 6.00 min (method 5). $^1$H NMR (400 MHz, CHLOROFORM-d) δ 8.36 (s, 1H), 7.97-7.91 (m, 2H), 7.22 (d, J=8.3 Hz, 2H), 5.32-5.29 (m, 1H), 4.77 (d, J=2.4 Hz, 1H), 4.66 (s, 1H), 4.61 (dd, J=2.4, 1.5 Hz, 1H), 3.93 (s, 3H), 3.21-3.13 (m, 1H), 3.12 (s, 3H), 3.07 (s, 3H), 2.64-2.54 (m, 1H), 2.50-2.43 (m, 1H), 2.13 (dd, J=17.1, 6.6 Hz, 1H), 2.01 (dd, J=11.0, 8.3 Hz, 1H), 1.95-1.85 (m, 1H), 1.82-1.75 (m, 1H), 1.73 (s, 4H), 1.50-1.36 (m, 10H), 1.26-1.21 (m, 1H), 1.18-1.13 (m, 1H), 1.10-1.10 (m, 1H), 1.08 (br. s., 1H), 1.03 (s, 3H), 1.00 (s, 3H), 0.99 (s, 3H), 0.94 (s, 6H).

Step 3. Preparation of methyl 4-((1R,3aS,5aR,5bR,7aR, 11aS,11bR,13aR,13bR)-5a,5b,8,8,11a-pentamethyl-1-(prop-1-en-2-yl)-3a-(1H-1,2,4-triazol-3-yl)-2,3,3a,4,5,5a, 5b,6,7,7a,8,11,11a,11b,12,13,13a,13b-octadecahydro-1H-cyclopenta[a]chrysen-9-yl)benzoate.

To a solution of methyl 4-((1R,3aS,5aR,5bR,7aR,11aS, 11bR,13aR,13bR)-3a-(formylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (115 mg, 0.192 mmol) in glacial acetic acid (2mL) and THF (1 mL) was added hydrazine hydrate (0.097 mL, 1.917 mmol). The resulting slurry was stirred at 90° C. After 3 h the reaction was cooled to rt and concentrated. The resulting residue was triturated with MeOH, filtered and washed with MeOH then dried under vacuo to give the title compound (104.3 mg, 0.175 mmol, 91% yield) as a white solid. LC/MS: m/e 596.3 (M+H)$^+$, 5.28 min (method 3). $^1$H NMR (400 MHz, CHLOROFORM-d) δ 8.05 (s, 1H), 7.93 (d, J=7.8 Hz, 2H), 7.19 (d, J=8.1 Hz, 2H), 5.29 (d, J=4.9 Hz, 1H), 4.82 (br. s., 1H), 4.66 (br. s., 1H), 3.91 (s, 3H), 3.18 (d, J=10.0 Hz, 1H), 2.43 (t, J=10.6 Hz, 1H), 2.32 (d, J=12.7 Hz, 1H), 2.17-2.05 (m, 2H), 1.94-1.82 (m, 3H), 1.77 (s, 3H), 1.71-1.62 (m, 3H), 1.53-1.30 (m, 10H), 1.17 (d, J=14.4 Hz, 3H), 1.06 (s, 3H), 0.95 (br. s., 3H), 0.92 (br. s., 6H), 0.78 (s, 3H).

The title compound was also obtained in the following manner:

To a solution of methyl 4-((1R,3aS,5aR,5bR,7aR,11aS,11bR,13aR,13bR)-3a-((E)-((dimethylamino)methylene)carbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (145 mg, 0.231 mmol) in glacial acetic acid (3 mL) was added hydrazine hydrate (0.058 mL, 1.156 mmol). The resulting slurry was stirred at 90° C. After 3 h, the reaction was let cooled to rt and concentrated. The residue was triturated with MeOH, filtered, washed with MeOH and dried in vacuo to give the title compound (91.2 mg, 66.2% yield) as white solid. The residue from the filtrate was purified by reverse phase prep-HPLC using HPLC method 2 and dried to give more of the title compound (31.4 mg, 22.78% yield) as a white solid. LC/MS: m/e 596.4 (M+H)$^+$, 5.26 min (method 3). $^1$H NMR (400 MHz, CHLOROFORM-d) δ 8.84 (br. s., 1H), 7.93 (d, J=8.6 Hz, 2H), 7.19 (d, J=8.3 Hz, 2H), 5.37-5.24 (m, 1H), 4.81 (s, 1H), 4.68 (s, 1H), 3.92 (s, 3H), 3.12 (dd, J=10.8, 6.1 Hz, 1H), 2.55-2.42 (m, 1H), 2.35 (d, J=13.2 Hz, 1H), 2.18-2.06 (m, 1H), 2.01-1.90 (m, 2H), 1.83 (d, J=13.2 Hz, 2H), 1.76 (s, 3H), 1.73-1.64 (m, 3H), 1.54-1.30 (m, 8H), 1.25-1.09 (m, 4H), 1.06 (s, 3H), 0.96 (s, 3H), 0.92 (s, 3H), 0.91 (s, 3H), 0.80 (s, 3H).

Step 4: To a solution of methyl 4-((1R,3aS,5aR,5bR,7aR,11aS,11bR,13aR,13bR)-5a,5b,8,8,11a-pentamethyl-1-(prop-1-en-2-yl)-3a-(1H-1,2,4-triazol-3-yl)-2,3,3a,4,5,5a,5b,6,7,7a,8,11,11a,11b,12,13,13a,13b-octadecahydro-1H-cyclopenta[a]chrysen-9-yl)benzoate (192 mg, 0.322 mmol) in THF (3 mL) and MeOH (1 mL) was added a solution of 3N lithium hydroxide (0.322 mL, 0.967 mmol). The reaction was stirred at 75° C. After 1.5 h the reaction was cooled to rt and concentrated to a viscous oil. The crude material was purified by reverse phase prep-HPLC using HPLC method 1 and dried in vacuo to give 4-((1R,3aS,5aR,5bR,7aR,11aS,11bR,13aR,13bR)-5a,5b,8,8,11a-pentamethyl-1-(prop-1-en-2-yl)-3a-(1H-1,2,4-triazol-3-yl)-2,3,3a,4,5,5a,5b,6,7,7a,8,11,11a,11b,12,13,13a,13b-octadecahydro-1H-cyclopenta[a]chrysen-9-yl)benzoic acid (134.4 mg, 68.8% yield) as a white solid. LC/MS: m/e 582.3 (M+H)$^+$, 4.68 min (method 3). $^1$H NMR (400 MHz, 1:1 CDL3: METHANOL-d$_4$) δ 8.57 (s, 1H), 7.89 (d, J=8.3 Hz, 2H), 7.17 (d, J=8.3 Hz, 2H), 5.26 (d, J=4.6 Hz, 1H), 4.77 (d, J=1.2 Hz, 1H), 4.62 (d, J=1.5 Hz, 1H), 3.15 (td, J=10.6, 4.5 Hz, 1H), 2.55 (td, J=12.2, 3.3 Hz, 1H), 2.28 (d, J=13.7 Hz, 1H), 2.10 (dd, J=17.1, 6.4 Hz, 1H), 1.90 (t, J=11.5 Hz, 1H), 1.86-1.75 (m, 3H), 1.73 (s, 3H), 1.70-1.62 (m, 3H), 1.52-1.28 (m, 8H), 1.25-1.18 (m, 1H), 1.17-1.08 (m, 3H), 1.04 (s, 3H), 0.95 (s, 3H), 0.89 (s, 6H), 0.78 (s, 3H). $^{13}$C NMR (101 MHz, 1:1 CDCl$_3$:METHANOL-d$_4$) δ 169.8, 163.0, 150.9, 149.5, 147.1, 145.6, 130.7, 129.4, 129.0, 124.7, 110.4, 78.5, 53.6, 50.8, 50.6, 50.3, 47.3, 43.3, 42.5, 41.3, 40.1, 38.4, 38.1, 37.0, 34.6, 34.3, 30.9, 29.9, 29.4, 26.3, 22.0, 21.5, 20.4, 19.8, 16.9, 16.0, 15.3.

Example 6

Preparation of 4-((1R,3aS,5aR,5bR,7aR,11aS,11bR,13aR,13bR)-3a-(1-(2-(1,1-dioxidothiomorpholino)ethyl)-1H-1,2,4-triazol-3-yl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

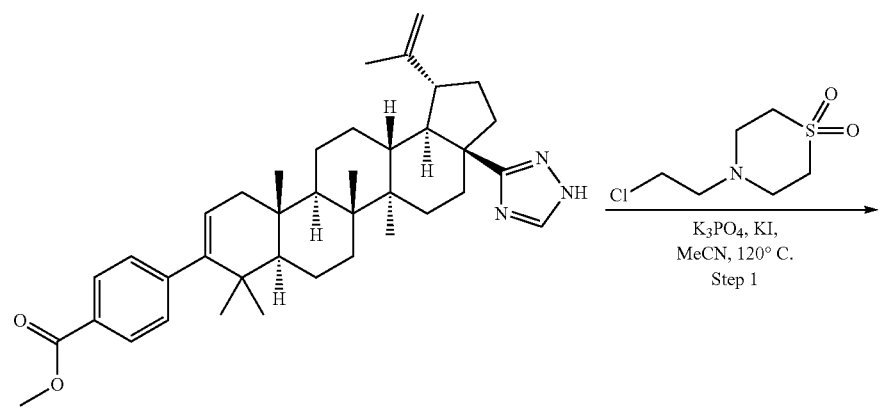

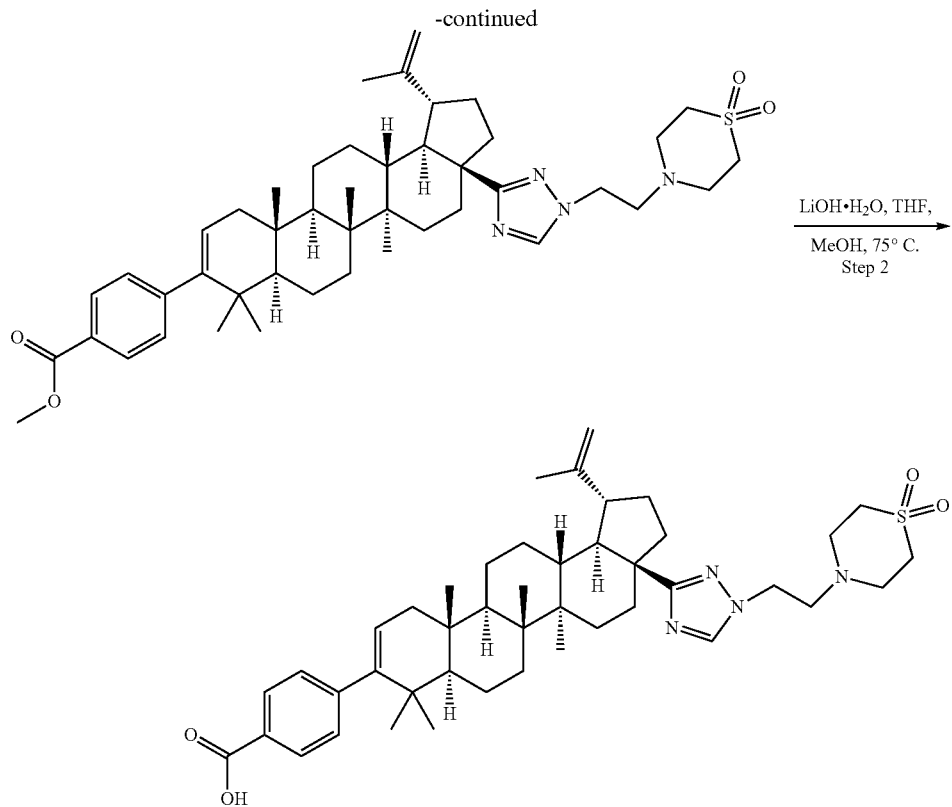

Example 6

Step 1. Preparation of methyl 4-((1R,3aS,5aR,5bR,7aR,11aS,11bR,13aR,13bR)-3a-(1-(2-(1,1-dioxidothiomorpholino)ethyl)-1H-1,2,4-triazol-3-yl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate, TFA.

Methyl 4-((1R,3aS,5aR,5bR,7aR,11aS,11bR,13aR,13bR)-5a,5b,8,8,11a-pentamethyl-1-(prop-1-en-2-yl)-3a-(1H-1,2,4-triazol-3-yl)-2,3,3a,4,5,5a,5b,6,7,7a,8,11,11a,11b,12,13,13a,13b-octadecahydro-1H-cyclopenta[a]chrysen-9-yl)benzoate (28 mg, 0.047 mmol), 4-(2-chloroethyl)thiomorpholine 1,1-dioxide (18.58 mg, 0.094 mmol), phosphoric acid, potassium salt (49.9 mg, 0.235 mmol), and potassium iodide (31.2 mg, 0.188 mmol) were combined in a medium pressure tube and charged with acetonitrile (2 mL). The resulting slurry was stirred at 120° C. After 16 h, LC/MS showed starting material left thus was added more 4-(2-chloroethyl)thiomorpholine 1,1-dioxide (18.58 mg, 0.094 mmol) and the mixture was further stirred continued at 120° C. for another 8 h. The reaction was cooled to rt, filtered, washed with DCM and concentrated to a brown solid. The crude material was purified by reverse phase prep-HPLC using HPLC method 1 and dried under vacuo to give methyl 4-((1R,3aS,5aR,5bR,7aR,11aS,11bR,13aR,13bR)-3a-(1-(2-(1,1-dioxidothiomorpholino)ethyl)-1H-1,2,4-triazol-3-yl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate, TFA (12.1 mg, 46% based on rec. sm) as a glassy solid. LC/MS: m/e 757.4 (M+H)$^+$, 5.50 min (method 3). $^1$H NMR (400 MHz, CHLOROFORM-d) δ 9.61 (br. s., 1H), 8.46 (br. s., 2H), 7.93 (d, J=8.3 Hz, 2H), 7.19 (d, J=8.3 Hz, 2H), 5.32-5.27 (m, 1H), 4.76 (s, 1H), 4.67 (s, 1H), 4.46 (t, J=5.4 Hz, 2H), 3.91 (s, 3H), 3.22-3.13 (m, 2H), 3.13-3.05 (m, 7H), 3.05-2.94 (m, 1H), 2.59-2.46 (m, 1H), 2.32 (d, J=13.4 Hz, 1H), 2.17-2.07 (m, 1H), 2.01-1.88 (m, 2H), 1.82 (d, J=13.4 Hz, 2H), 1.74 (s, 3H), 1.72-1.64 (m, 2H), 1.57-1.34 (m, 8H), 1.27-1.19 (m, 2H), 1.13 (dd, J=12.7, 3.7 Hz, 1H), 1.06 (s, 3H), 0.97 (s, 3H), 0.92 (s, 6H), 0.82 (s, 3H).

Step 2. To a solution of methyl 4-((1R,3aS,5aR,5bR,7aR,11aS,11bR,13aR,13bR)-3a-(1-(2-(1,1-dioxidothiomorpholino)ethyl)-1H-1,2,4-triazol-3-yl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate, TFA (12.1 mg, 0.014 mmol) in THF (1 mL) and MeOH (0.25 mL) was added a solution of 1N lithium hydroxide (0.056 mL, 0.056 mmol). The reaction was stirred at 75° C. After 1 h, the reaction was cooled to rt and purified by reverse phase HPLC using HPLC method 5 to give 4-((1R,3aS,5aR,5bR,7aR,11aS,11bR,13aR,13bR)-3a-(1-(2-(1,1-dioxidothiomorpholino)ethyl)-1H-1,2,4-triazol-3-yl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid, TFA (11.3 mg, 91% yield) as a white solid. LC/MS: m/e 743.4 (M+H)$^+$, 4.80 min (method 3). $^1$H NMR (400 MHz, CHLOROFORM-d) δ 9.24 (s, 1H), 7.99 (d, J=8.3 Hz, 2H), 7.23 (d, J=8.3 Hz, 2H), 5.31 (d, J=4.6 Hz, 1H), 4.76 (s, 1H), 4.66 (s, 1H), 4.40 (t, J=5.7 Hz, 2H), 3.17-3.10 (m, 2H), 3.09-3.04 (m, 8H), 3.03-2.99 (m, 1H), 2.54 (td, J=12.2, 3.3 Hz, 1H), 2.34 (d, J=13.7 Hz, 1H), 2.13 (dd, J=17.2, 6.2 Hz, 1H), 2.01-1.86 (m, 2H), 1.84-1.79 (m, 1H), 1.75 (s, 3H), 1.73-1.59 (m, 3H), 1.57-1.34 (m, 8H), 1.31-1.17 (m, 3H), 1.16-1.08 (m, 2H), 1.06 (s, 3H), 0.97 (s, 3H), 0.94 (s, 6H), 0.81 (s, 3H). ¹³C NMR (101 MHz, CHLOROFORM-d) δ 183.4, 170.4, 164.3, 161.7, 150.0, 149.5, 146.3, 143.0, 130.2, 129.1, 127.0, 124.0, 110.1, 77.2 (br. s., 1C), 63.3, 55.3, 52.8, 51.1 (d, J=2.3 Hz, 1C), 50.6, 49.6, 49.4, 48.5, 46.7, 42.6, 41.7, 40.7, 39.2, 37.6, 37.5, 36.3, 33.5 (br. s., 1C), 30.1, 29.4, 28.6, 25.4, 21.4, 21.1, 19.7, 19.3, 16.5, 15.6, 14.8.

Example 7

Preparation of 4-((1R,3aS,5aR,5bR,7aR,11aS,11bR, 13aR,13bR)-5a,5b,8,8,11a-pentamethyl-3a-(1-methyl-1H-1,2,4-triazol-5-yl)-1-(prop-1-en-2-yl)-2, 3,3a,4,5,5a,5b,6,7,7a,8,11,11a,11b,12,13,13a,13b-octadecahydro-1H-cyclopenta[a]chrysen-9-yl) benzoic acid Step 1. Preparation of 4-((1R,3aS,5aR,5bR,7aR,11aS,11bR, 13aR,13bR)-5a,5b,8,8,11a-pentamethyl-3a-(1-methyl-1H-1,2,4-triazol-5-yl)-1-(prop-1-en-2-yl)-2,3,3a,4,5,5a,5b,6,7, 7a,8,11,11a,11b,12,13,13a,13b-octadecahydro-1H-cyclopenta[a]chrysen-9-yl)benzoate.

To a solution mixture of methyl 4-((1R,3aS,5aR,5bR,7aR, 11aS,11bR,13aR,13bR)-3a-(E)-((dimethylamino)methylene)carbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (60 mg, 0.096 mmol) and methyl 4-((1R,3aS,5aR,5bR,7aR, 11aS,11bR,13aR,13bR)-3a-(formylcarbamoyl)-5a,5b,8,8, 11a-pentamethyl-1-(prop-1-en-2-yl)-2,3,3a,4,5,5a,5b,6,7, 7a,8,11,11a,11b,12,13,13a,13b-octadecahydro-1H-cyclopenta[a]chrysen-9-yl)benzoate (57.4 mg, 0.096 mmol) in glacial acetic acid (2 mL) was added methylhydrazine

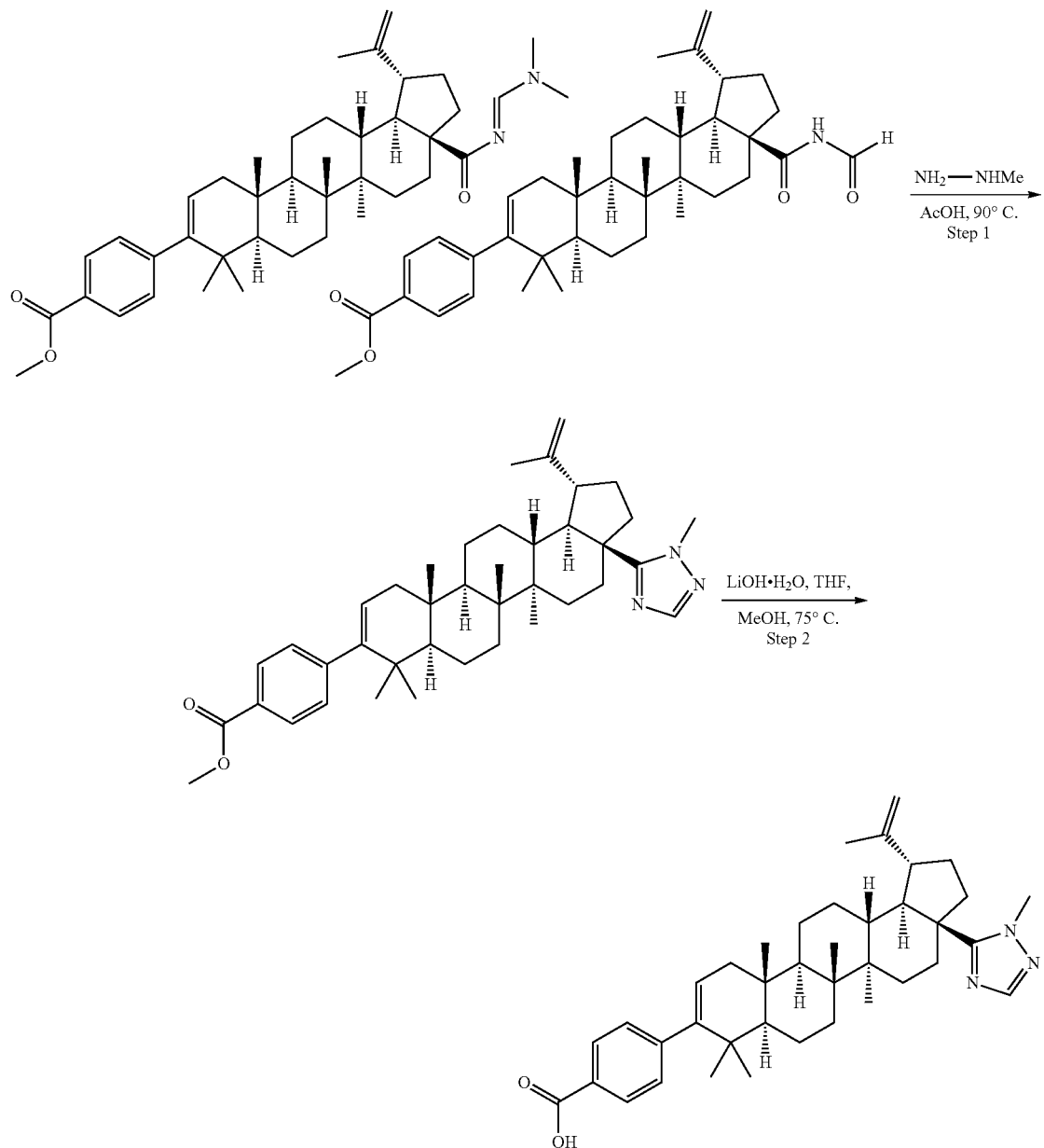

Example 7

(0.036 mL, 0.670 mmol). The reaction was stirred at 90° C. After 16 h, the reaction was cooled to rt and concentrated to a brown viscous oil. Crude material was purified by reverse phase prep-HPLC using HPLC method 2 and dried in vacuo to give the title compound (12.7 mg, 21.76% yield) as a white solid. LC/MS: m/e 610.3 (M+H)$^+$, 6.61 min (method 3). $^1$H NMR (400 MHz, CHLOROFORM-d) δ 8.18 (s, 1H), 7.93 (d, J=8.6 Hz, 2H), 7.20 (d, J=8.6 Hz, 2H), 5.30 (dd, J=6.2, 1.8 Hz, 1H), 4.82 (d, J=1.5 Hz, 1H), 4.70-4.65 (m, 1H), 4.02 (s, 3H), 3.91 (s, 3H), 3.16 (td, J=11.1, 4.5 Hz, 1H), 2.86 (td, J=12.3, 3.4 Hz, 1H), 2.39-2.31 (m, 1H), 2.14 (dd, J=17.1, 6.4 Hz, 1H), 2.06-1.99 (m, 1H), 1.98-1.90 (m, 1H), 1.84-1.77 (m, 1H), 1.75 (s, 3H), 1.72-1.64 (m, 3H), 1.63-1.53 (m, 2H), 1.52-1.38 (m, 7H), 1.38-1.30 (m, 1H), 1.24-1.16 (m, 2H), 1.05 (s, 3H), 1.02 (d, J=1.5 Hz, 1H), 0.97 (s, 3H), 0.92 (s, 6H), 0.83 (s, 3H).

Step 2: To a solution of methyl 4-((1R,3aS,5aR,5bR,7aR,11aS,11bR,13aR,13bR)-5a,5b,8,8,11a-pentamethyl-3a-(1-methyl-1H-1,2,4-triazol-5-yl)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (12.7 mg, 0.021 mmol) in THF (1 mL) and MeOH (0.25 mL) was added a solution of 1N lithium hydroxide (0.073 mL, 0.073 mmol). The reaction was stirred at 75° C. After 1 h, the reaction was cooled to rt and purified by reverse phase prep-HPLC using HPLC method 4 and dried in vacuo to give 4-((1R,3aS,5aR,5bR,7aR,11aS,11bR,13aR,13bR)-5a,5b,8,8,11a-pentamethyl-3a-(1-methyl-1H-1,2,4-triazol-5-yl)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid (9.1 mg, 0.015 mmol, 70.4% yield) as a white solid. LC/MS: m/e 596.3 (M+H)$^+$, 5.33 min (method 3). $^1$H NMR (400 MHz, 1:1 CDCl$_3$:METHANOL-d$_4$) δ 7.89 (d, J=8.3 Hz, 2H), 7.78 (s, 1H), 7.17 (d, J=8.6 Hz, 2H), 5.30-5.22 (m, 1H), 4.77 (d, J=1.7 Hz, 1H), 3.93 (s, 3H), 3.23-3.05 (m, 2H), 2.33 (d, J=13.7 Hz, 1H), 2.11 (dd, J=17.2, 6.2 Hz, 1H), 2.04-1.96 (m, 1H), 1.93-1.80 (m, 2H), 1.72 (s, 3H), 1.68 (d, J=16.4 Hz, 1H), 1.63-1.58 (m, 1H), 1.55-1.30 (m, 10H), 1.28-1.19 (m, 2H), 1.18-1.08 (m, 2H), 1.04 (s, 3H), 0.97 (s, 3H), 0.90 (s, 6H), 0.82 (s, 3H).

HIV cell culture assay—MT-2 cells and 293T cells were obtained from the NIH AIDS Research and Reference Reagent Program. MT-2 cells were propagated in RPMI 1640 media supplemented with 10% heat inactivated fetal bovine serum, 100 μg/mL penicillin G and up to 100 units/mL streptomycin. The 293T cells were propagated in DMEM media supplemented with 10% heat inactivated fetal bovine serum (FBS), 100 units/mL penicillin G and 100 μg/mL streptomycin. The proviral DNA clone of NL$_{4-3}$ was obtained from the NIH AIDS Research and Reference Reagent Program. A recombinant NL$_{4-3}$ virus, in which a section of the nef gene from NL4-3 was replaced with the *Renilla* luciferase gene, was used as a reference virus. In addition, residue Gag P373 was converted to P373S. Briefly, the recombinant virus was prepared by transfection of the altered proviral clone of NL$_{4-3}$. Transfections were performed in 293T cells using LipofectAMINE PLUS from Invitrogen (Carlsbad, Calif.), according to manufacturer's instruction. The virus was titered in MT-2 cells using luciferase enzyme activity as a marker. Luciferase was quantitated using the Dual Luciferase kit from Promega (Madison, Wis.), with modifications to the manufacturer's protocol. The diluted Passive Lysis solution was pre-mixed with the re-suspended Luciferase Assay Reagent and the re-suspended Stop & Glo Substrate (2:1:1 ratio). Fifty (50) μL of the mixture was added to each aspirated well on assay plates and luciferase activity was measured immediately on a Wallac TriLux (Perkin-Elmer). Antiviral activities of inhibitors toward the recombinant virus were quantified by measuring luciferase activity in cells infected for 4-5 days with NLRluc recombinants in the presence serial dilutions of the inhibitor. The EC$_{50}$ data for the compounds is shown in Table 1. Biological Data Key for EC$_{50}$

| Compounds with EC$_{50}$ > 0.1 μM | Compounds with EC$_{50}$ ≤ 0.1 μM |
| --- | --- |
| Group "B" | Group "A" |

TABLE 1

| Example # | Structure | WT EC50 μM |
| --- | --- | --- |
| 1 | 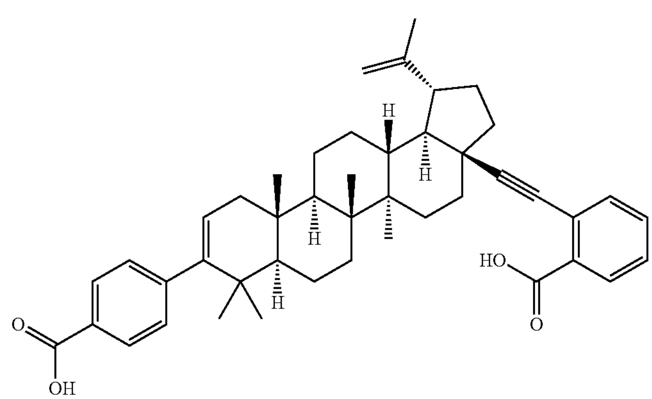 | 0.08 |

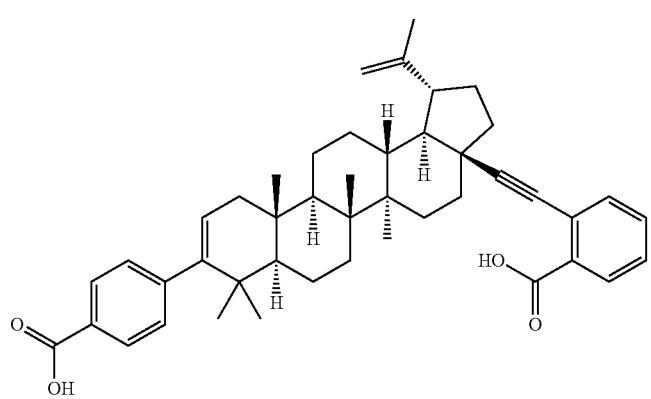

TABLE 1-continued

| Example # | Structure | WT EC50 μM |
|---|---|---|
| 2 | 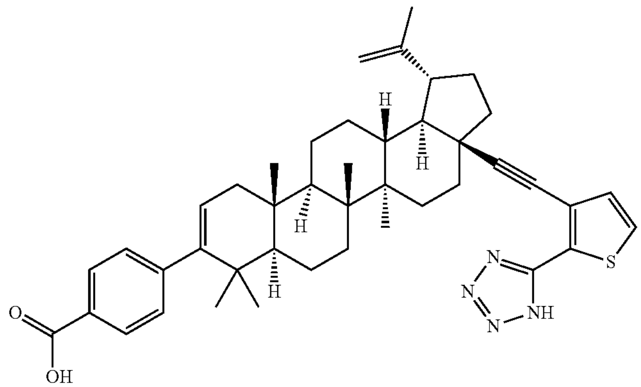 | B |
| 3 | 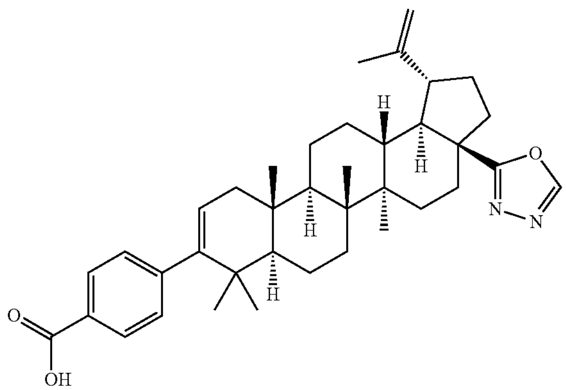 | A |
| 4 | 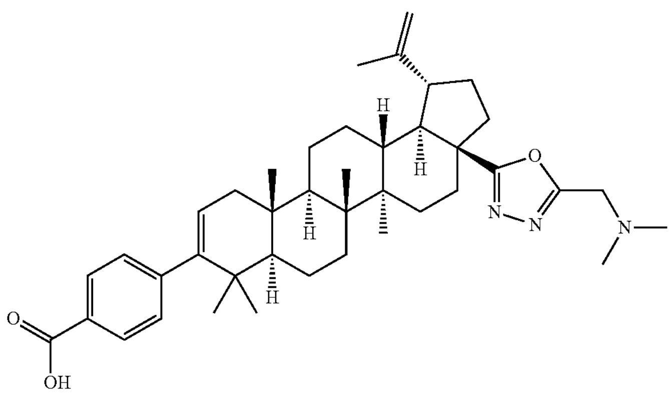 | A |
| 5 | 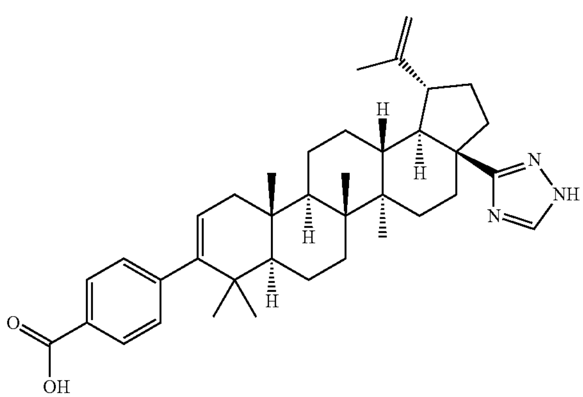 | A |

TABLE 1-continued

| Example # | Structure | WT EC50 µM |
|---|---|---|
| 6 | (structure shown) | A |
| 7 | (structure shown) | A |

The foregoing description is merely illustrative and should not be understood to limit the scope or underlying principles of the invention in any way. Indeed, various modifications of the invention, in addition to those shown and described herein, will become apparent to those skilled in the art from the following examples and the foregoing description. Such modifications are also intended to fall within the scope of the appended claims.

What is claimed is:

1. A compound of Formula I:

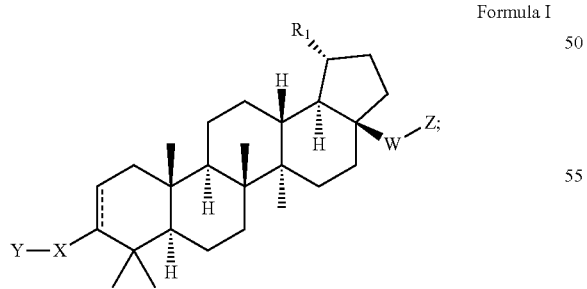

Formula I or a pharmaceutically acceptable salt thereof; wherein $R_1$ is isopropenyl or isopropyl;

X is selected from the group of phenyl, heteroaryl, $C_{4-8}$ cycloalkyl, $C_{4-8}$ cycloalkenyl, $C_{4-9}$ spirocycloalkyl, $C_{4-9}$ spirocycloalkenyl, $C_{4-8}$oxacycloalkyl, $C_{6-8}$ dioxacycloalkenyl, $C_{6-9}$ oxaspirocycloalkyl and $C_{6-9}$ oxaspirocycloalkenyl ring;

wherein X is substituted with A, wherein A is at least one member selected from the group of —H, -halo, -hydroxyl, —$C_{1-6}$ alkyl, —$C_{1-6}$ alkoxy, —$C_{1-6}$haloalkyl, —CN, —COOR$_2$, —CONR$_2$R$_2$, —NR$_8$R$_9$, and —$C_{1-6}$ alkyl-Q, Q is selected from the group of aryl, heteroaryl, substituted heteroaryl, —OR$_2$, —COORS, —NR$_2$R$_2$, —SO$_2$R$_7$, —CONHSO$_2$R$_3$, and —CONHSO$_2$NR$_2$R$_2$;

$R_2$ is —H, —$C_{1-6}$ alkyl, -alkylsubstituted $C_{1-6}$ alkyl or benzyl;

Y is selected from the group of —COOR$_2$, —C(O) NR$_2$SO$_2$R$_3$, —C(O )NHSO$_2$NR$_2$R$_2$, —NR$_2$SO$_2$R$_2$, —SO$_2$NR$_2$R$_2$, —$C_{3-6}$ cycloalkyl-COOR$_2$, —$C_{2-6}$ alkenyl-COOR$_2$, —$C_{2-6}$ alkynyl-COOR$_2$, —$C_{1-6}$ alkyl-COOR$_2$, -alkylsubstituted-$C_{1-6}$ alkyl —COOR$_2$, —CF$_2$—COOR$_2$, —NHC(O)(CH$_2$)n—COOR$_2$, —SO$_2$NR$_2$C(O)R$_2$, -tetrazole, and —CONHOH, wherein n=1-6;

W is absent or is .C≡C.;

Z is a heteroaryl group, wherein Z can be substituted with —H, —$C_{1-6}$ alkyl, —$C_{1-6}$ substituted alkyl, —$C_{1-6}$ alkyl-Q$_1$, —CONR$_{10}$R$_{11}$, and —COOR$_2$;

Q$_1$ is selected from the group of heteroaryl, substituted heteroaryl, halogen, —CF$_3$, —OR$_2$, —COOR$_2$, —NR$_4$R$_5$, —CONR$_{10}$R$_{11}$ and —SO$_2$R$_7$;

$R_3$ is —H, —$C_{1-6}$ alkyl, -alkylsubstituted $C_{1-6}$ alkyl or benzyl;

$R_4$ is selected from the group of —H, —$C_{1-6}$ alkyl, —$C_{1-6}$ alkyl-C(OR$_3$)$_2$—$C_{3-6}$ cycloalkyl, —$C_{1-6}$ substituted alkyl, —$C_{1-6}$ alkyl-$C_{3-6}$ cycloalkyl, —$C_{1-6}$ alkyl-Q$_1$, —$C_{1-6}$ alkyl-$C_{3-6}$ cycloalkyl-$Q_1$, aryl, heteroaryl, substituted heteroaryl, —$COR_6$, —$COCOR_6$, —$SO_2R_7$, and —$SO_2NR_2R_2$;

$R_5$ is selected from the group of —H, —$C_{1-6}$ alkyl, —$C_{3-6}$ cycloalkyl, —$C_{1-6}$ alkylsubstituted alkyl, —$C_{1-6}$ alkyl-$NR_8R_9$, —$COR_{10}$, —$COR_6$, —$COCOR_6$, —$SO_2R_7$ and —$SO_2NR_2R_2$;

or $R_4$ and $R_5$ are taken together with the adjacent N to form a cycle selected from the group of:

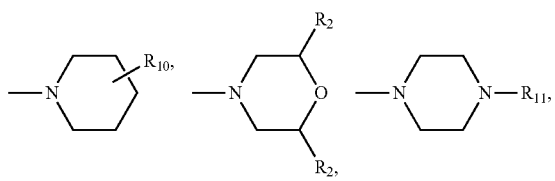

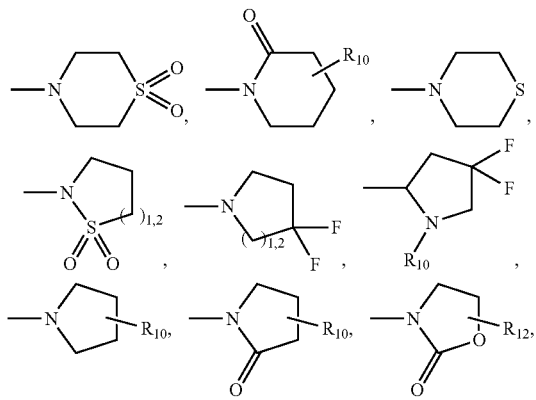

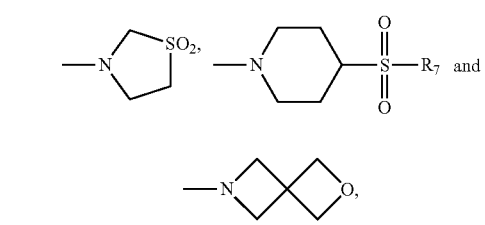

with the proviso that only one of $R_4$ or $R_5$ can be selected from the group of —$COR_6$, —$COCOR_6$, —$SO_2R_7$ and —$SO_2NR_2R_2$;

$R_6$ is selected from the group of —H, —$C_{1-6}$ alkyl, —$C_{1-6}$ alkyl-substitutedalkyl, —$C_{3-6}$ cycloalkyl, —$C_{3-6}$ substitutedcycloalkyl-$Q_2$, —$C_{1-6}$ alkyl-$Q_2$, —$C_{1-6}$ alkyl-substitutedalkyl-$Q_2$, —$C_{3-6}$ cycloalkyl-$Q_2$, aryl-$Q_2$, —$NR_2R_2$, and —$OR_3$;

$Q_2$ is selected from the group of aryl, heteroaryl, substituted heteroaryl, —$OR_2$, —$COOR_2$, —$NR_8R_9$, $SO_2R_7$, —$CONHSO_2R_3$, and —$CONHSO_2NR_2R_2$;

$R_7$ is selected from the group of —H, —$C_{1-6}$ alkyl, —$C_{1-6}$ substituted alkyl, —$C_{3-6}$ cycloalkyl, —$CF_3$, aryl, and heteroaryl;

$R_8$ and $R_9$ are independently selected from the group of —H, —$C_{1-6}$ alkyl, —$C_{1-6}$ substituted alkyl, aryl, heteroaryl, substituted aryl, substituted heteroaryl, —$C_{1-6}$ alkyl-$Q_2$, and —$COOR_3$, or $R_8$ and $R_9$ are taken together with the adjacent N to form a cycle selected from the group of:

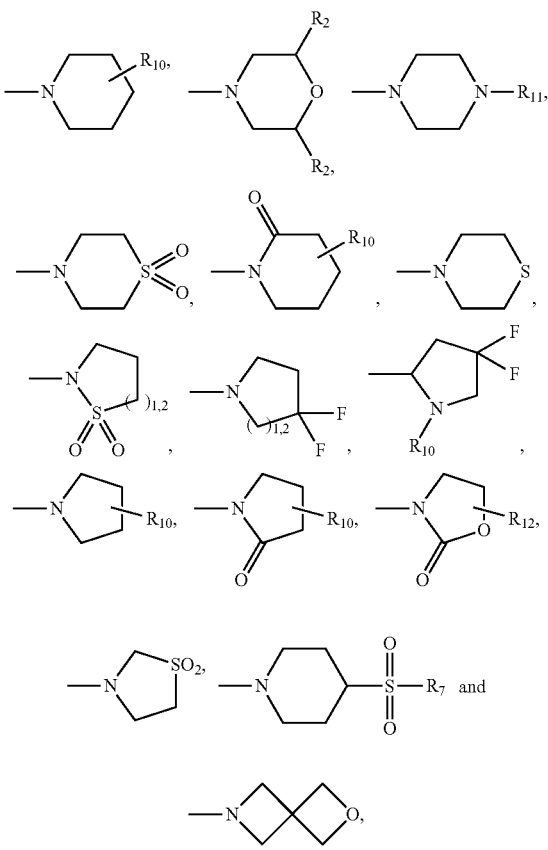

with the proviso that only one of $R_8$ or $R_9$ can be —$COOR_3$;

$R_{10}$ is selected from the group of —H, —$C_{1-6}$ alkyl, —$NR_2R_2$, and —$COOR_3$;

$R_{11}$ is selected from the group of —H, —$C_{1-6}$ alkyl, —$C_{1-6}$ alkyl-OH; —$C_{1-6}$ alkyl, —$C_{1-6}$ substituted alkyl,—$C_{3-6}$ cycloalkyl, —$COR_7$, —$COONR_2R_2$, —$SOR_7$, and —$SONR_2R_2$; and $R_{12}$ is selected from the group of —H, —$C_{1-6}$ alkyl, —$COOR_3$, and aryl.

2. A compound or salt as claimed in claim 1, wherein X is phenyl.

3. A compound or salt as claimed in claim 2, wherein Y is —COOH.

4. A compound selected from the group consisting of:

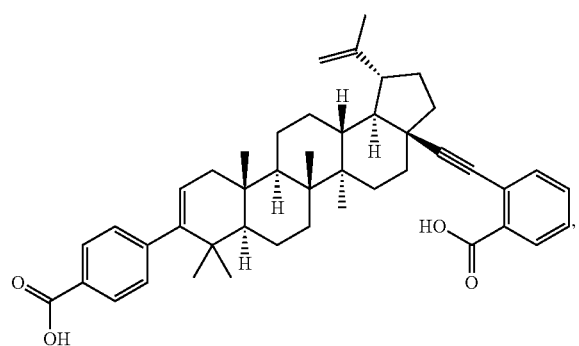

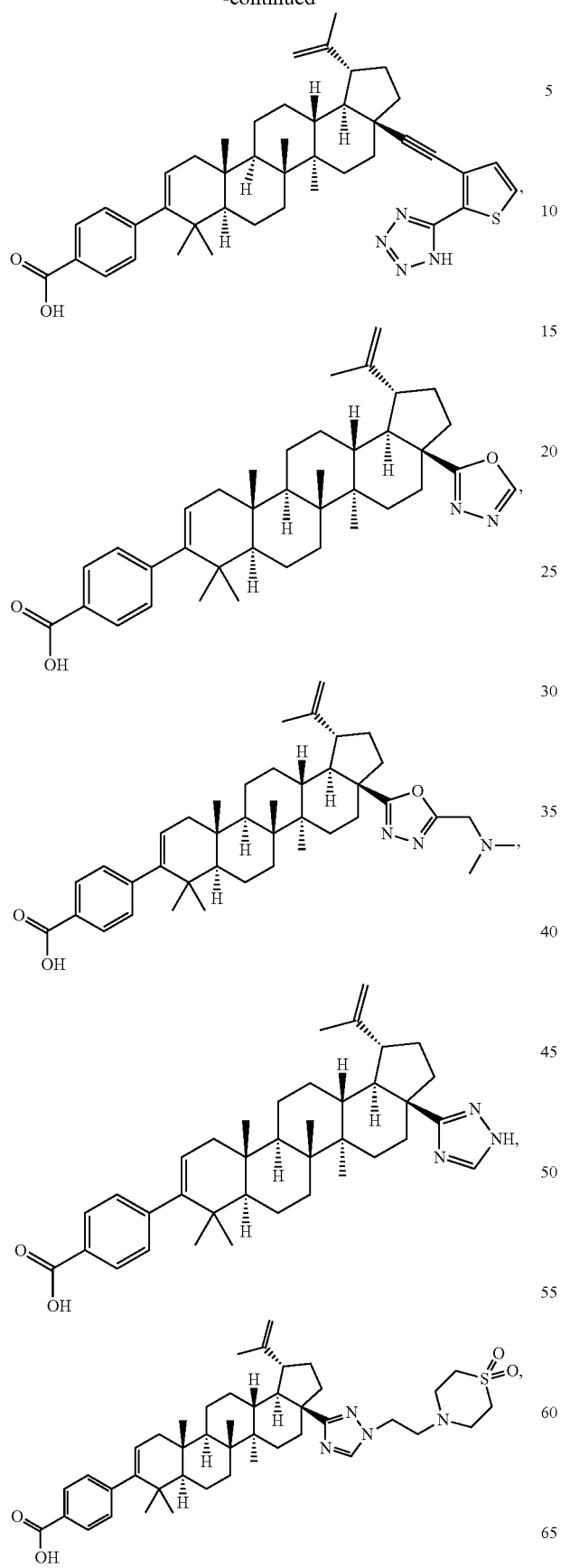
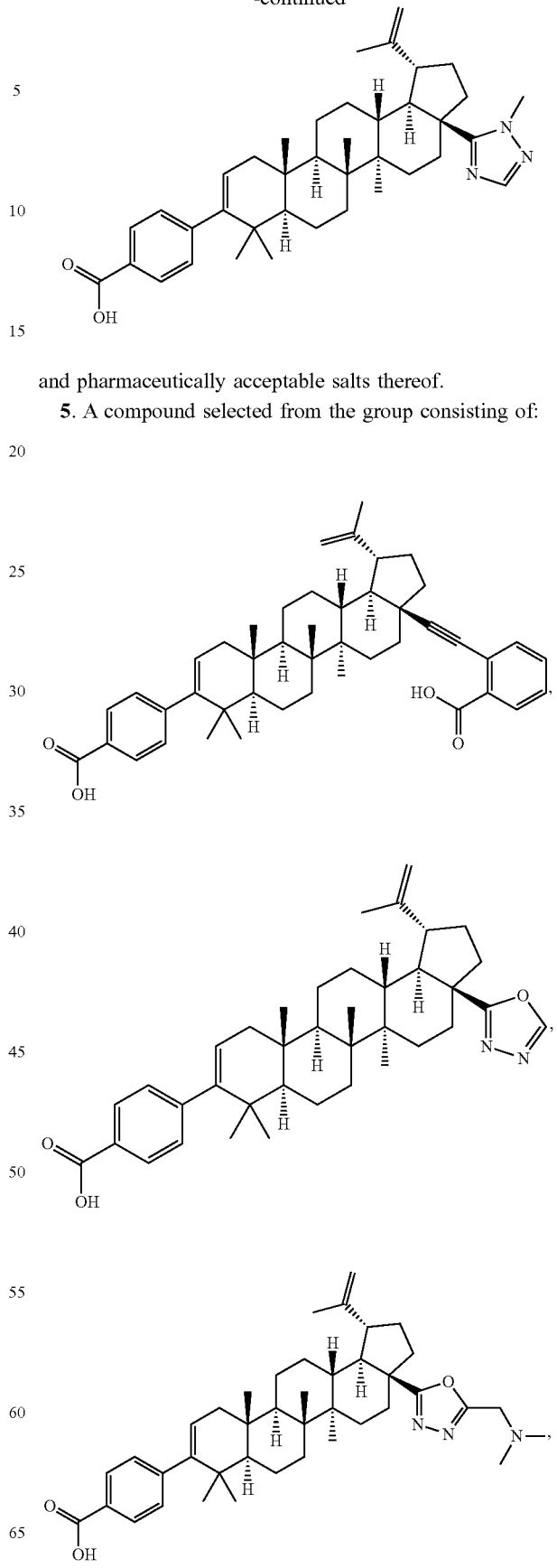
and pharmaceutically acceptable salts thereof.
5. A compound selected from the group consisting of:

67

-continued

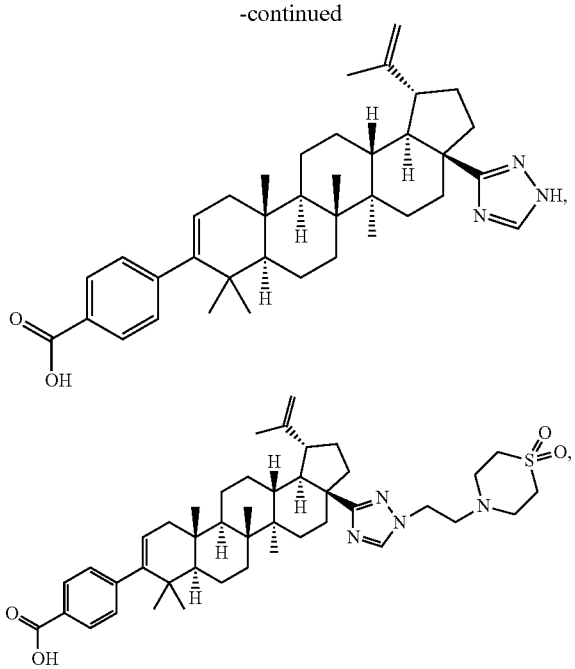

68

-continued

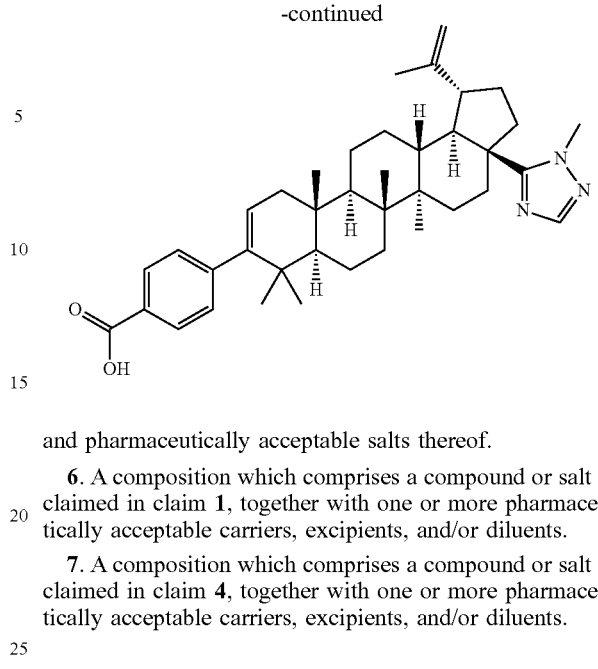

and pharmaceutically acceptable salts thereof.

6. A composition which comprises a compound or salt as claimed in claim 1, together with one or more pharmaceutically acceptable carriers, excipients, and/or diluents.

7. A composition which comprises a compound or salt as claimed in claim 4, together with one or more pharmaceutically acceptable carriers, excipients, and/or diluents.

* * * * *